(12) United States Patent
Moore

(10) Patent No.: US 8,216,313 B2
(45) Date of Patent: Jul. 10, 2012

(54) SPONDYLOLISTHESIS CORRECTION APPARATUS AND METHOD

(76) Inventor: Mark R. Moore, Westlake, LA (US)

(*) Notice: Subject to any disclaimer, the term of this patent is extended or adjusted under 35 U.S.C. 154(b) by 379 days.

(21) Appl. No.: 12/459,221

(22) Filed: Jun. 29, 2009

(65) Prior Publication Data

US 2010/0016968 A1    Jan. 21, 2010

Related U.S. Application Data

(63) Continuation-in-part of application No. 11/821,717, filed on Jun. 25, 2007, now Pat. No. 7,744,649.

(51) Int. Cl.
*A61F 2/44* (2006.01)

(52) U.S. Cl. .................. 623/17.11; 623/17.16

(58) Field of Classification Search .... 623/17.11–17.16; 606/60, 246–249, 57, 282, 90, 105, 327, 606/320, 313, 62–64

See application file for complete search history.

(56) References Cited

U.S. PATENT DOCUMENTS

| | | | |
|---|---|---|---|
| 3,486,505 A | 12/1969 | Morrison | |
| 4,714,469 A | 12/1987 | Kenna | |
| 4,863,476 A | 9/1989 | Shepperd | |
| 5,601,556 A | 2/1997 | Pisharodi | |
| 6,086,589 A | 7/2000 | Kuslich et al. | |
| 6,126,660 A | 10/2000 | Dietz | |
| 6,159,212 A | 12/2000 | Schoedinger, III et al. | |
| 6,251,111 B1 | 6/2001 | Barker et al. | |
| 6,491,695 B1 | 12/2002 | Roggenbuck | |
| 6,533,791 B1 | 3/2003 | Betz et al. | |
| 6,582,431 B1 | 6/2003 | Ray | |
| 6,679,915 B1 | 1/2004 | Cauthen | |
| 6,755,841 B2 | 6/2004 | Fraser et al. | |
| 6,899,716 B2 | 5/2005 | Cragg | |
| 6,921,403 B2 | 7/2005 | Cragg et al. | |
| 7,014,633 B2 | 3/2006 | Cragg | |
| 2006/0009767 A1 | 1/2006 | Kiester | |

*Primary Examiner* — Eduardo C Robert
*Assistant Examiner* — Ellen C Hammond
(74) *Attorney, Agent, or Firm* — Shultz & Associates, P.C.

(57) ABSTRACT

An apparatus and method are provided that allow for the realignment and stabilization of adjacent vertebrae. An implant of this invention both repositions adjacent vertebrae and remains in situ to maintain a new position. The implant has an upper half and a lower half, which are interlocked such that they can slide horizontally with respect to each other. Movement of the implant halves and their respective positions are controlled by a reduction bar and reduction rod in combination with an internal locking block within the implant. The reduction rod, being connected to a lower half and placed adjacent to the upper half, is rotated to bring the implant halves into alignment. The internal locking block engages to permanently hold the alignment and maintain the new position. A release mechanism for the internal locking block allows for readjustment of the implant halves and realignment of the vertebrae.

24 Claims, 27 Drawing Sheets

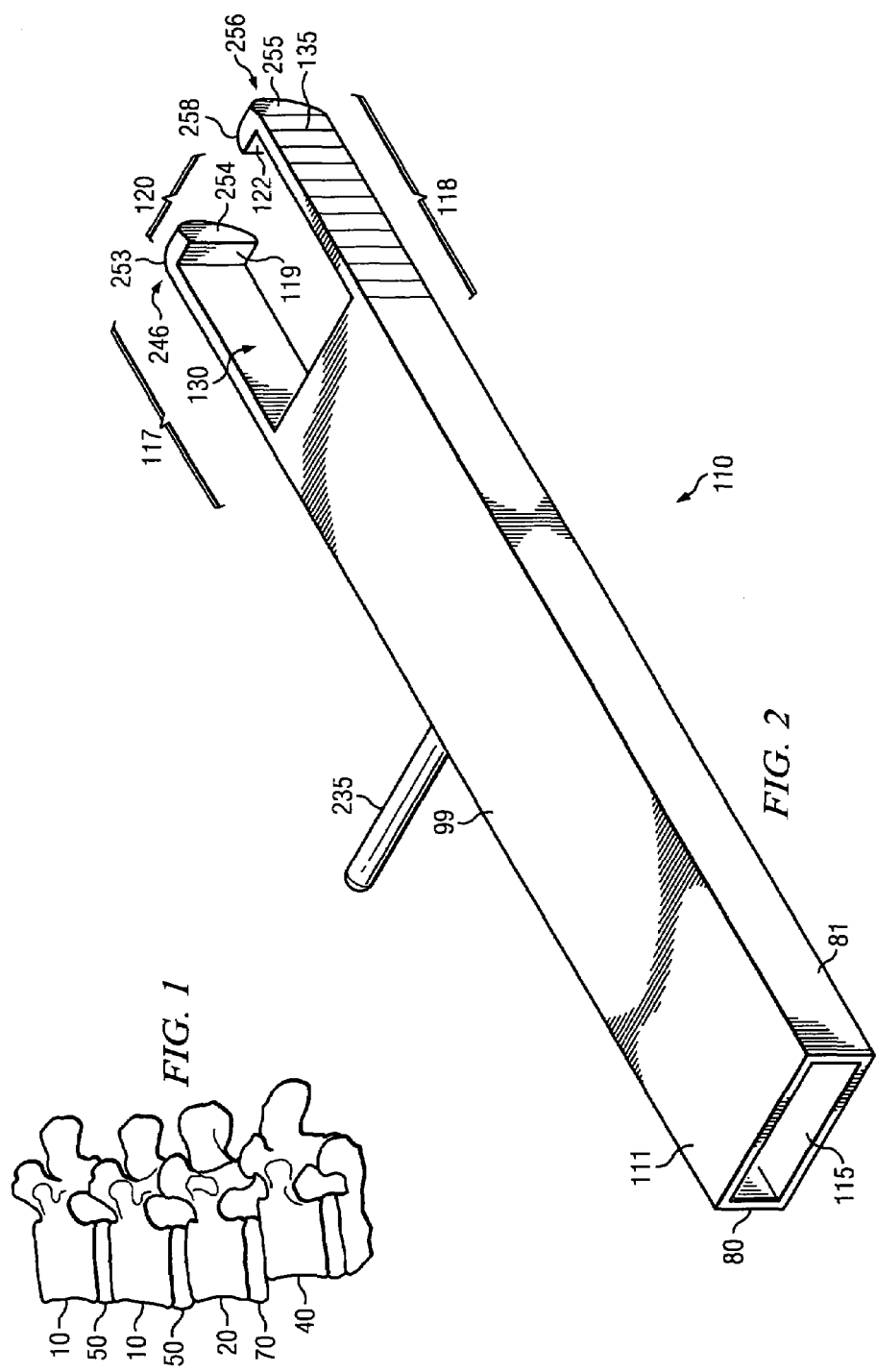

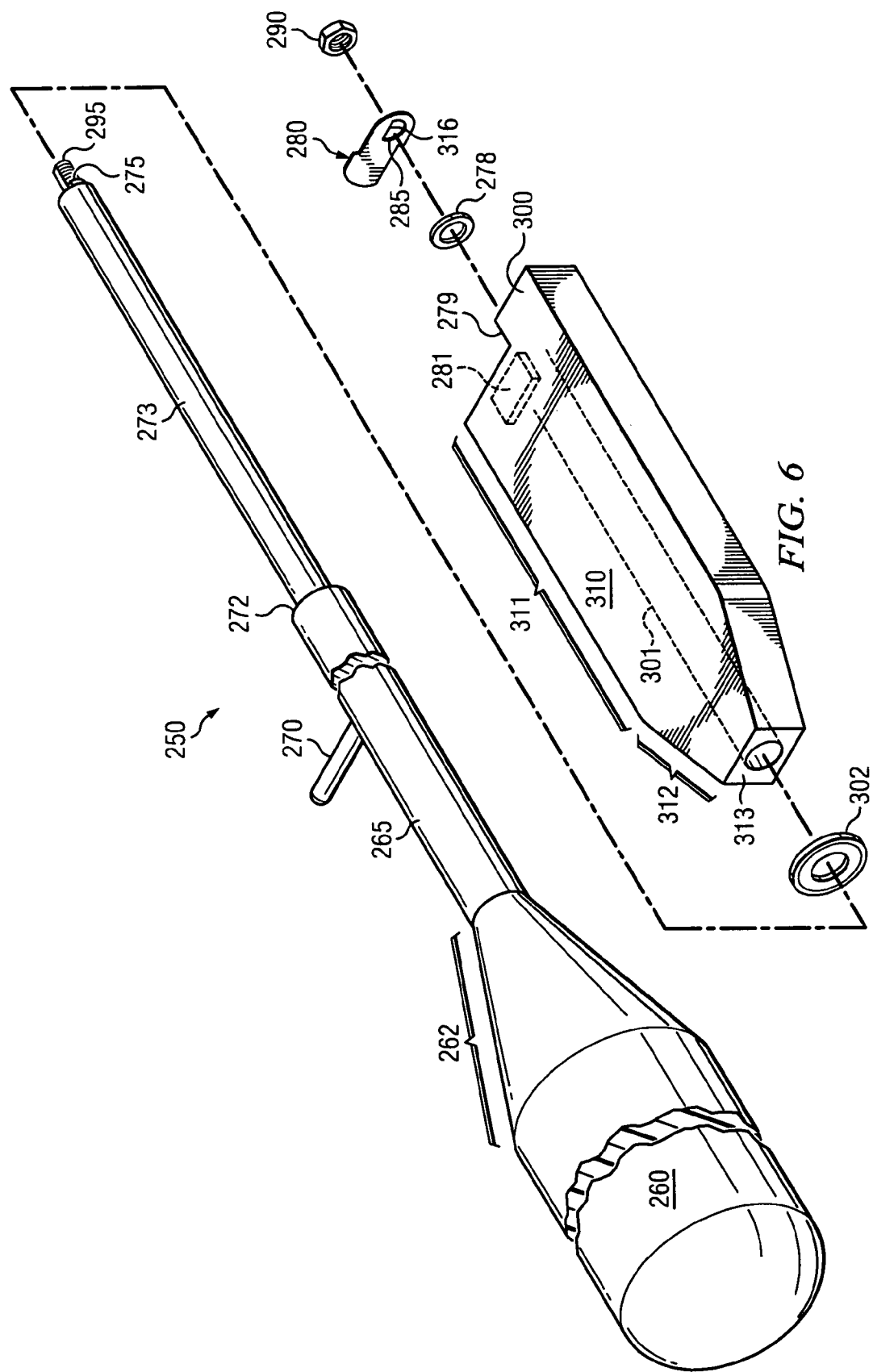

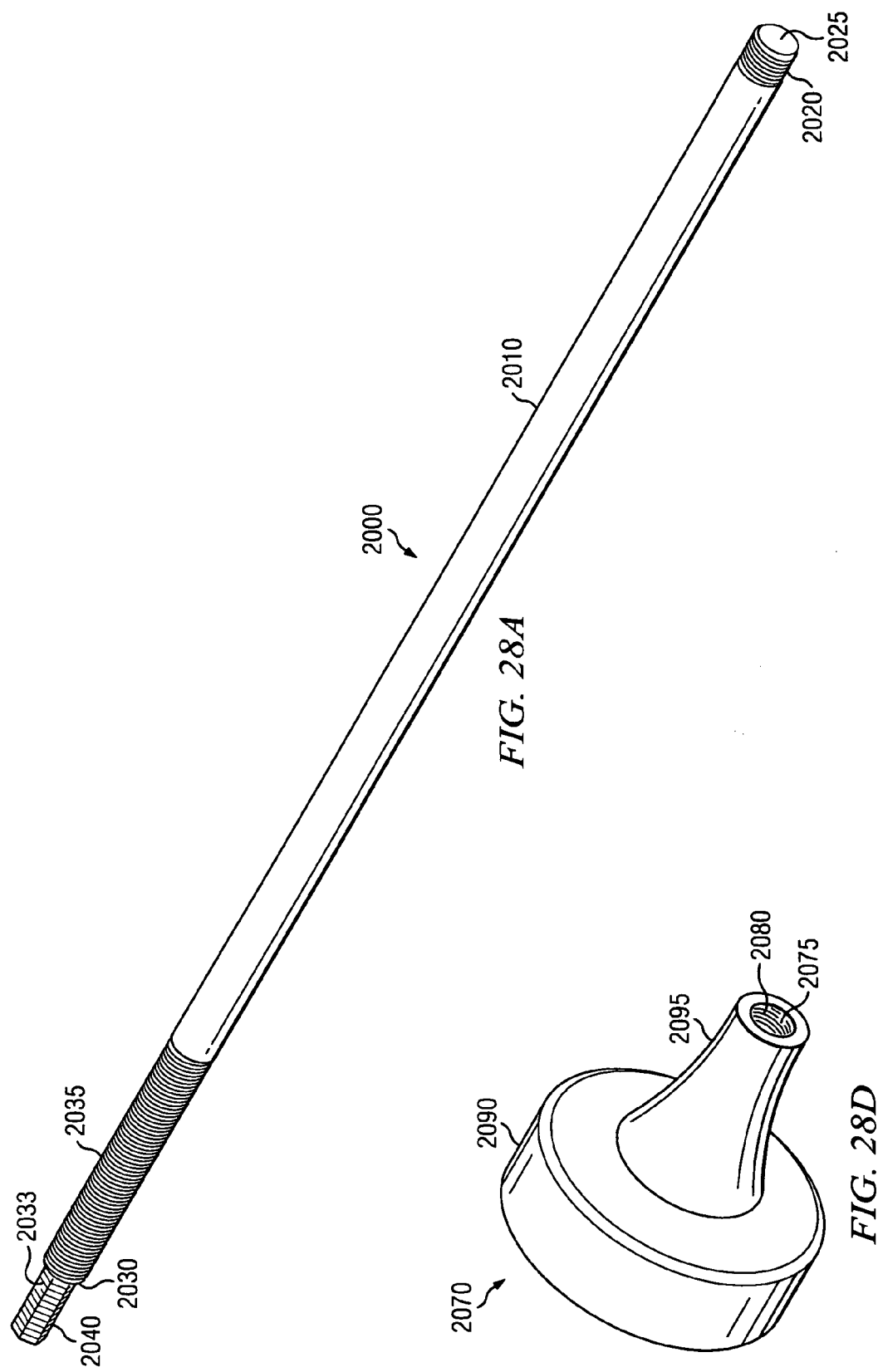

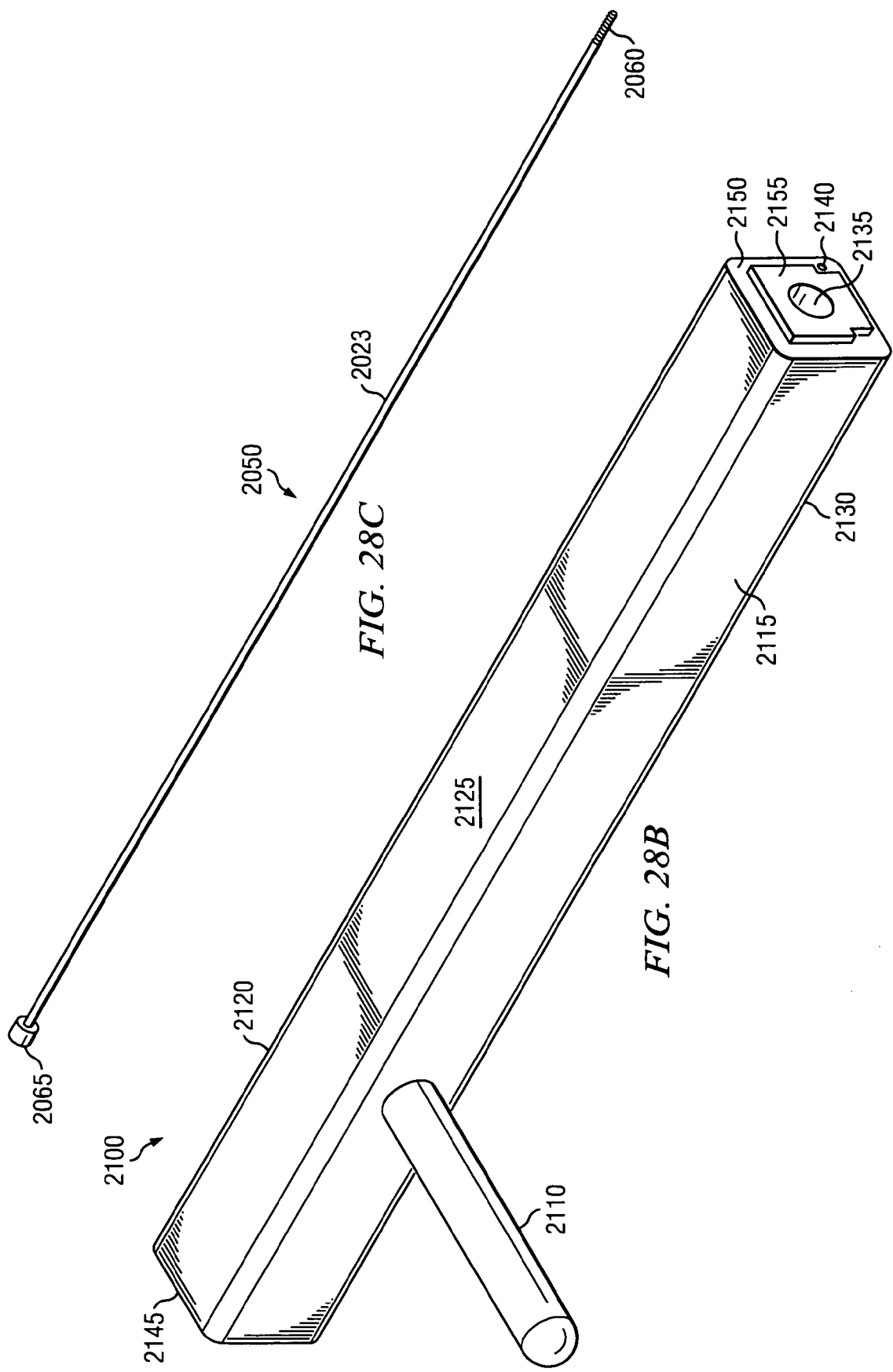

SPONDYLOLISTHESIS CORRECTION APPARATUS AND METHOD

CROSS-REFERENCE TO RELATED APPLICATIONS

This application is a Continuation-In-Part claiming priority benefit from U.S. patent application Ser. No. 11/821,717, now U.S. Pat. No. 7,744,649, entitled "Spondylolisthesis Correction Apparatus and Method" filed on Jun. 25, 2007.

FIELD OF INVENTION

The present invention relates generally to the correction of spondylolisthesis and other spinal column injuries or deformities in the fields of neurosurgery and orthopedics. More specifically, the invention is used for the stabilization of repositioned vertebral bodies.

BACKGROUND OF THE INVENTION

Spondylolisthesis is a medical condition in which one vertebra slips forward in relation to an adjacent vertebra usually in the lumbar region of the spine. This condition can cause symptoms that include pain in the low back, thighs, and/or legs, muscle spasms, weakness, and/or tight hamstring muscles while in some cases only radiographic imaging reveals the condition.

To correct this condition and other similar conditions of vertebral dislocation, the only effective long-term curative treatment is reconstructive surgery and fusion of the affected vertebra to its adjacent neighbor. Vertebral fusion is generally accomplished by fixing apparatus to and between vertebrae. In addition to the stabilization and correction of spondylolisthesis, other spinal conditions may be: stabilization of fractures, correction of spinal deformities (e.g. scoliosis, kyphosis), stabilization and correction of degenerative spinal lesions and narrow spinal canal, reconstruction after tumor resection, and secondary spinal surgery.

The novel method and implant discussed herein allows for the correction of spondylolisthesis by movement of the vertebrae into better alignment while maintaining stabilization of the vertebrae in the new position in order for the spinal fusion to be completed by ossification. Specifically, the implant is used to move the vertebrae into a post-surgical position and keep the vertebrae in the post-surgical position during the ossification process.

Roggenbuck in U.S. Pat. No. 6,491,695 discloses the use of an apparatus and method for aligning vertebrae which involves creating a helical threaded surface in endcaps of the vertebrae and then threading a positioning device into position to align the vertebrae. Once the vertebrae are positioned, the positioning device is removed and an implant is inserted to maintain the vertebrae in position.

Ray in U.S. Pat. No. 6,582,431 discloses the use of an expandable non-threaded spinal fusion device which requires the vertebrae to be moved into correct position before the device can be inserted and implanted.

Betz in U.S. Pat. No. 6,533,791 discloses a device for stabilization of the lumbar spinal column which requires cutting helical thread marks into the vertebrae that are to be repositioned and then installing an implant to maintain the position. The repositioning device does not stay in the body after the surgery but instead an implant must be inserted to maintain the repositioning.

Therefore, there is a need in the art to combine an implant with a repositioning device in order to reduce the possible repositioning of the vertebrae. There is a further need in the art to provide for adjustment of the vertebrae after an implant has been installed.

SUMMARY OF INVENTION

Disclosed is an apparatus and method for aligning vertebrae due to slippage of the vertebrae relative to each other. To this end, a method and apparatus is disclosed for placing a novel implant between two vertebrae which will move the vertebrae into proper alignment and maintain that alignment until ossification can occur. The implant disclosed is left in situ once the vertebrae have been repositioned. The implant disclosed also provides support for the effected vertebrae superior to that of previous methods known in the prior art. The implant also allows for fine adjustments and post implantation adjustments of the vertebrae superior to that of the prior art.

The disclosed method includes approaching the vertebra anteriorly and removing a portion of vertebral disk between the misaligned vertebrae. Known interbody spacers are then inserted between the vertebrae until the proper restorative height is achieved. The spacers are removed and a distractor is placed between the vertebrae in order to guide the subsequent placement of the implant. A novel gate is inserted over a novel distractor to properly guide a novel saw mechanism to cut into the vertebrae at precise locations and allow for the insertion of a novel implant. Different gates are provided depending on the necessary restorative height to be achieved and amount of slip between the vertebrae.

The disclosed implant has two halves which include a dovetail groove system which locks the two halves together but allows them to slide with respect to each other along their longitudinal axis. The implant has radial anchors which extend from each half and which fit into slots in the vertebrae cut by the saw. The implant includes a drive bolt which engages the two halves and which, when turned, slides one half of the implant in relation to the other. The advancing halves of the implant carry the radial anchors with them that align the vertebrae. Depending on the amount of slip between the vertebrae and the necessary restorative height, different sized implants and associated tools may be used.

The implant is inserted through a distractor by use of an inserter. The halves of the implant are aligned so that the radial anchors correspond to slots made in the misaligned vertebrae. The implant is rotated into place by the inserter such that the radial anchors fit securely in the slots previously made by the saw in the vertebrae. The distractor is then removed.

In the case of anterior listhesis of the superior vertebra, the drive bolt of the implant is then rotated so that the upper half of the implant is advanced posteriorly. The superior vertebra is pulled posteriorly with respect to the inferior vertebra by the movement of the upper half of the implant with respect to the lower half.

In an alternative embodiment, the implant body is rectangular and contains a locking block, a spring and internal chambers to lock the aligned implant in place.

The position of the implant is locked into place by use of an articulating combination of a nut and a plate, thereby maintaining alignment of the vertebrae. The nut and plate can be removed, allowing for post-surgical adjustment of the implant.

BRIEF DESCRIPTION OF DRAWINGS

The disclosed inventions will be described with reference to the accompanying drawings, which show important sample embodiments of the invention and which are incorporated in the specification hereof by reference, wherein:

FIG. 1 is a side view of a section of human spine characterized by a spondylolisthesis condition.

FIG. 2 is an isometric view of a distractor of a preferred embodiment of the invention.

FIG. 6 is an exploded isometric view of a saw of a preferred embodiment of the invention.

FIG. 28a is an isometric view of a reduction bar of a preferred embodiment of the invention.

FIG. 28b is an elevated view of a reduction rod of a preferred embodiment of the invention.

FIG. 28c is an elevated view of a thumbscrew of a preferred embodiment of the invention.

FIG. 28d is an isometric view of a reduction wheel of a preferred embodiment of the invention.

DETAILED DESCRIPTION OF PREFERRED EMBODIMENTS

Figure 3A:
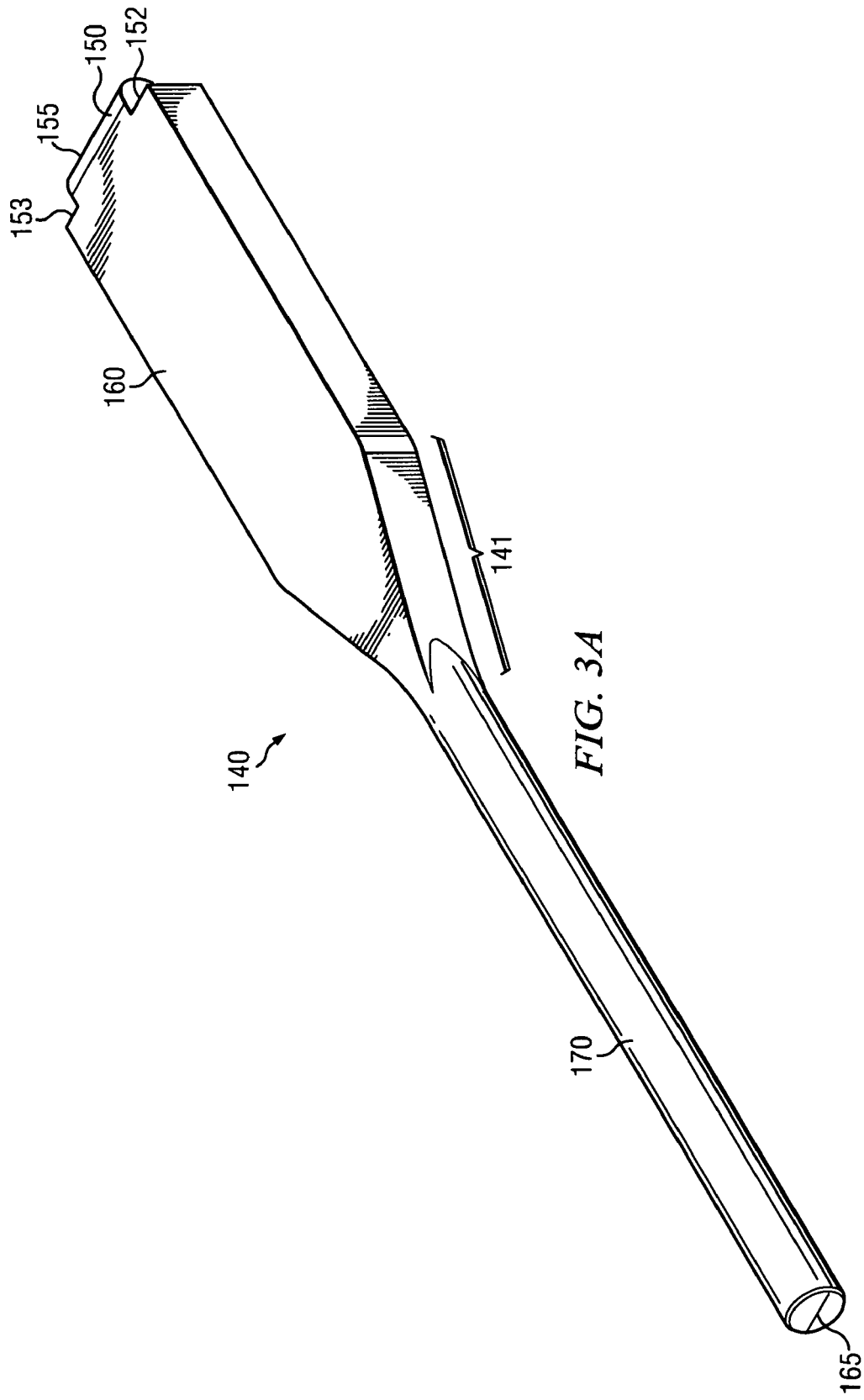
FIG. 3a is an isometric view of an impactor of a preferred embodiment of the invention.

FIG. 1 is an illustration of a lumbar spine in a patient who has contracted spondylolisthesis. The vertebrae 10 are separated by vertebral disk 50. As a result of advanced spondylolisthesis, superior vertebra 20 slips forward in relation to the next inferior vertebra 40 and causes distended disk 70. To repair slippage of the vertebrae, superior vertebra 20 and inferior vertebra 40 are realigned and fused together. To accomplish this, a portion of distended disk 70 is removed and replaced with an implant which maintains realignment and supports the spine until ossification occurs whereby superior vertebra 20 and inferior vertebra 40 are permanently fused.

In order to assure proper alignment, a magnetic resonance image ("MRI") or plain lateral radiographs are used to observe the supine position to measure the severity of the spondylolisthesis condition prior to surgery. The restorative height of the interbody space after partial removal of distended disk 70 and the necessary amount of re-alignment can be estimated by review of the MRI or plain lateral radiographs. The implant size can be determined by the estimates.

The present invention uses the anterior surgical approach to the lumbar spine in order to reach the vertebrae that will receive the implant. The anterior surgical approach to the lumbar spine is understood in the art and is not discussed in detail here.

Referring still to FIG. 1, once the lumbar spine is exposed to the surgeon, superior vertebra 20, inferior vertebra 40, and distended disk 70 are located and identified. A standard marking pin known in the art is inserted into distended disk 70 at the putative midline and left in place.

The implant should be optimally placed at the midline in the sagital plane. Lateral radiographs or x-rays are utilized to confirm the appropriate surgical level and anterior-posterior x-ray imaging demonstrates the midline relative to the marking pin. Once confirmed, the midline of distended disk 70 is marked on distended disk 70 by use of generally accepted marking means. The marking pin is then removed.

Portion of distended disk 70 is removed. Boundaries of generous rectangular annulatomy are created in distended disk 70 by use of scalpel. The size of the annulatomy will depend upon the size of the implant and allows additional space on either side of implant to allow interbody arthodesis on both sides of implant after implant is deployed. The width of annulatomy will be in the range of between about 2 cm and about 5 cm. Portion of distended disk 70 within the boundary of annulatomy is removed by use of rongeurs and curettes.

Vertebral endplate preparation is performed in standard fashion as known in the art while maintaining cortical endplate integrity centrally. Anterior osteophytes may also be removed from the ventral aspect of the vertebral bodies during this stage of the surgery.

In order to gain the appropriate restorative height between superior vertebra 20 and inferior vertebra 40, sequentially larger interbody spreaders are impacted into the rectangular annulotomy in distended disk 70 until optimal height restoration is achieved. Interbody spreaders are known in the art. When optimal height restoration is achieved, interbody spreaders are removed and appropriate height distractor 110 is inserted.

FIG. 2 illustrates one embodiment of distractor 110. Distractor 110 is made of titanium, stainless steel, or other commercially available material which is easily sterilized. Rigid plastics can be used such as polyvinyl chloride (PVC) in disposable embodiments. Distractor 110 is rectangular in cross-section and includes hollow distractor channel 115. Distractor channel 115 is rectangular in cross-section and runs the length of distractor 110. The dimensions of distractor 110 vary depending on the optimal height restoration to be achieved, but height of distractor 110 should generally range between about 0.5 cm and about 1.5 cm and the width of distractor 110 should range between about 2 cm and about 5 cm. The length of distractor 110 is between about 30 cm and about 60 cm. The thickness of walls of distractor 110 should range between about 1 mm and about 5 mm depending on the material of construction to achieve a rigid structure. The dimensions of distractor channel 115 should range between about 0.4 cm and about 1.4 cm high, about 1.9 cm and about 4.9 cm wide.

Posterior end of distractor 110 contains distractor arm 117 and distractor arm 118. Distractor arm 117 extends longitudinally from side 80 of distractor 110. Distractor arm 117 includes distractor point guide 246 having angled surfaces 253 and 254. Opposing angled surfaces 253 and 254 is distractor stop 119. Distractor arm 118 extends longitudinally from the side 81 of distractor 110 and includes distractor point guide 256 having rounded surfaces 258 and 255. Opposing rounded surfaces 258 and 255 is distractor stop 122. The height of distractor arm 117 and distractor arm 118 are approximately the same as the height of distractor 110. The width of distractor arm 117 and distractor arm 118 are between about 0.5 mm and about 1 mm. The width of the distractor arms should provide rigidity with respect to the body of the distractor. Distractor arm 118 and distractor arm 117 form implant hollow 130. End gap 120 is formed at the forward end of implant hollow 130. The preferred design of end gap 120 is between about 1.7 cm and about 4.7 cm. Distractor stop 122 and distractor stop 119 are between about 0.5 mm and about 2 mm in length.

Torque handle 235 is rigidly mounted to distractor body 99. Torque handle 235 is generally in the range of about 2 cm to about 5 cm in length with a diameter in the range of about 0.5 cm to about 2 cm. The preferred location of torque handle 235 is approximately between ¼ to ½ from the anterior end 111 of distractor 110. A set of distractor graticules 135 are etched at 1 mm intervals on the side of distractor 110 along the outside of distractor arm 118 and distractor arm 117.

In the preferred embodiment, the cross-sectional height and width of distractor 110 may vary. In its preferred use, a set of variable height distractors is provided so that the distractor height which matches the vertical distance between the vertebrae may be used during surgery. The preferred set of heights preferably varies in one millimeter increments between about 5 mm and about 2 cm.

FIG. 3a illustrates the preferred embodiment of impactor 140. Impactor 140 includes impactor handle 170 which is cylindrical with a diameter in the range of about 0.3 cm and about 2 cm. The length of impactor handle 170 ranges between about 5 cm and about 25 cm. In one embodiment, impactor handle 170 is etched with impactor centerline 165 across its diameter. Impactor centerline 165 is parallel to the long cross-sectional axis of impactor body 160.

Impactor body 160 is formed integrally with impactor handle 170. Impactor body 160 is rectangular in cross-section and sized to fit within distractor channel 115 without excessive play. In the preferred embodiment, the impactor body is sized to allow for approximately 0.3 mm play between the exterior of the impactor body and the distractor channel.

Angled section 141 extends from impactor handle 170 to impactor body 160 at an angle between about 25 and about 65 degrees. Angled section 141 serves to center the impactor handle with respect to the impactor body and distribute impact loads from the impactor handle to the impactor body as will be further described. The preferred length of impactor body 160 should range between about 30 cm and about 45 cm. The posterior end of impactor body 160 includes impactor seat 150 integrally formed with impactor body 160. Impactor seat 150 is sized and shaped to fit within end gap 120 shown in FIG. 2. Impactor seat 150 has rounded surface 155. On either side of impactor seat 150 are stop surface 152 and stop surface 153. Impactor 140 is preferably made from titanium, stainless steel, or other materials which are readily sterilized or from a rigid plastic such as PVC which may be disposed of after use.

Other cross-sectional shapes of the impactor and distractor are also acceptable, such as elliptical, as long as the impactor fits inside the distractor channel such that it can move longitudinally in distractor channel 115 without rotation and without significant "play" or angular displacement.

Figure 3B:
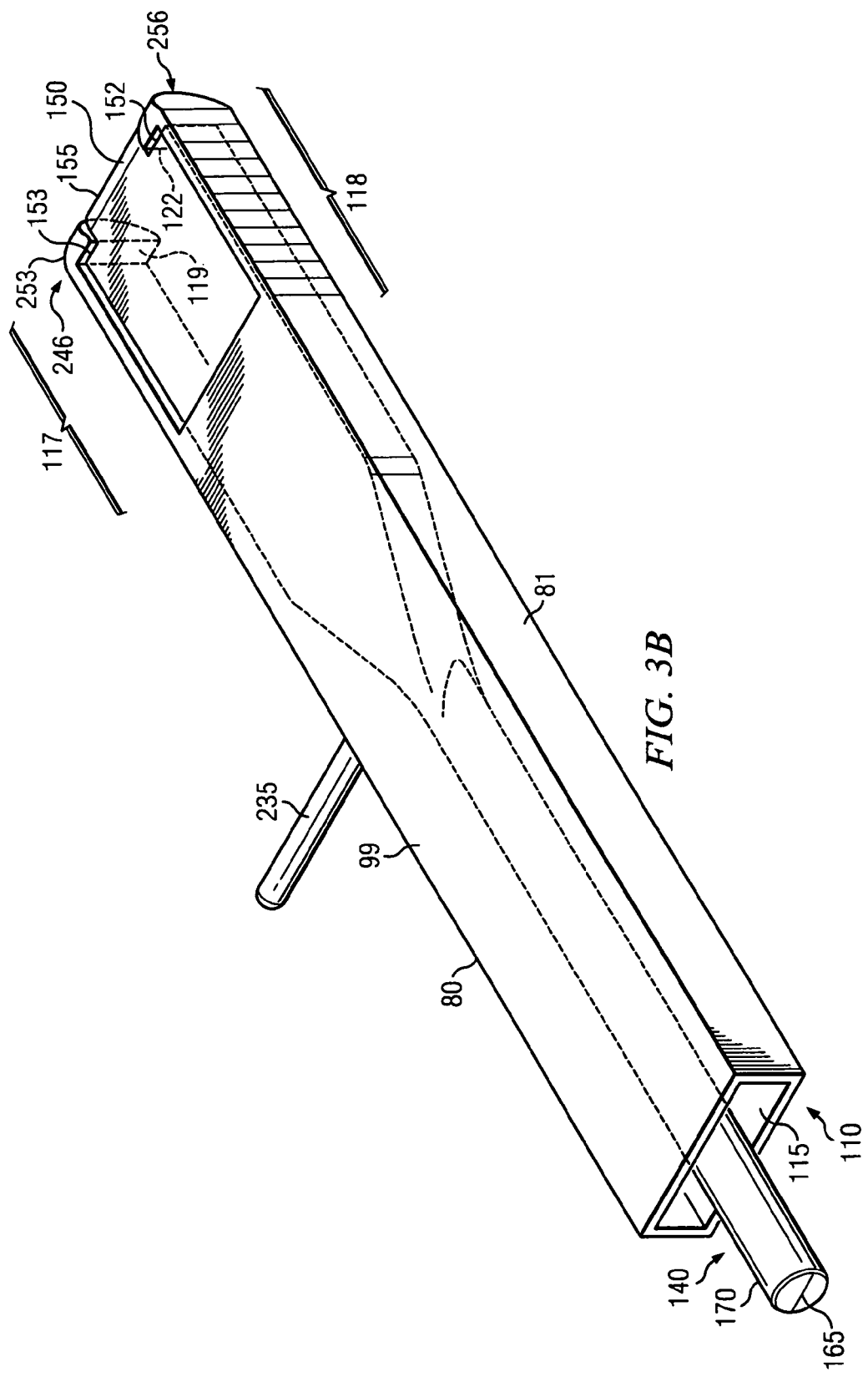
FIG. 3b is an isometric view of an impactor in conjunction with a distractor of a preferred embodiment of the invention.

In use, impactor 140 is placed inside distractor channel 115, such that impactor seat 150 fits into end gap 120 as shown in FIG. 3b. Impactor centerline 165 is aligned with the anatomical midline marked previously. Distractor 110 and impactor 140 are aligned with the anatomical midline and inserted into the rectangular annulatomy in distended disk 70. A mallet is used to tap impactor 140 and distractor 110 into the midline sagital plane under fluoroscopic guidance until posterior edge of distractor 110 reaches the dorsal epiphyseal ring on the ventrally superior vertebra 20. Impactor 140 is then withdrawn from distractor channel 115 and distractor 110 is left in situ.

In the preferred embodiment, impactor 140 is also provided in a set of variable sizes to match the set of variable sizes of distractor 110, as previously described.

Figure 4:
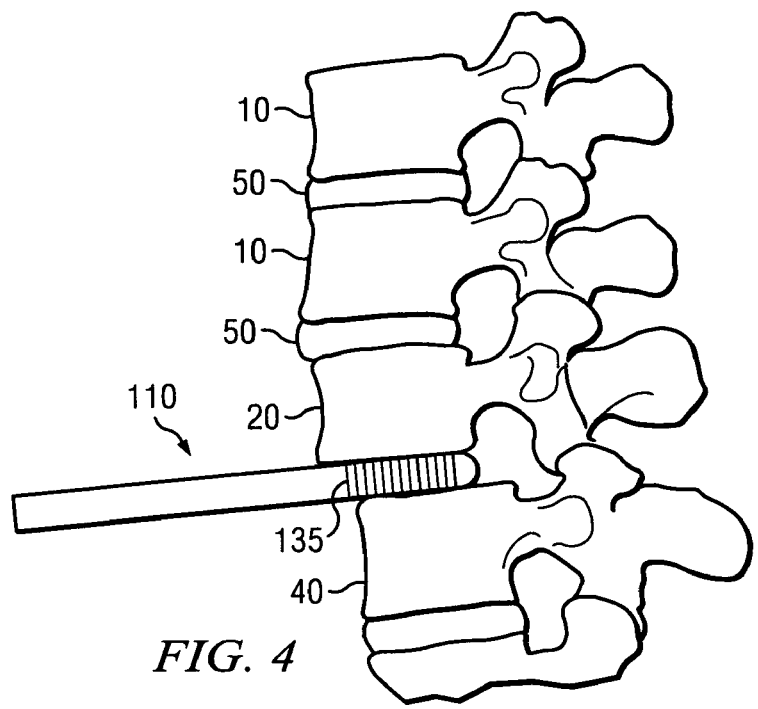
FIG. 4 is a side view of a section of a human spine with the distractor in place between vertebrae.

FIG. 4 shows distractor 110 in situ between superior vertebra 20 and inferior vertebra 40. Distractor 110 is between superior vertebra 20 and inferior vertebra 40. Once in position, distractor graticules 135 are used to gauge the amount of slip existing between superior vertebra 20 and inferior vertebra 40.

Figure 5A:
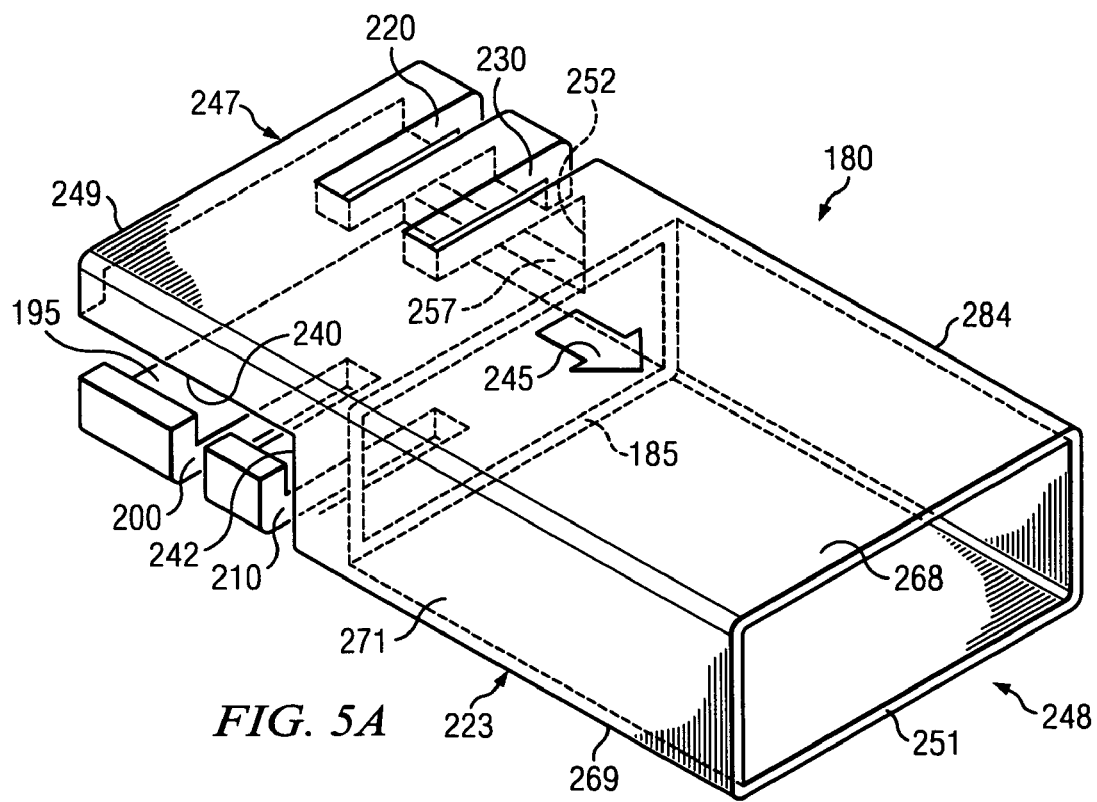
FIG. 5a is a partial isometric view of a gate of a preferred embodiment of the invention.
Figure 5B:
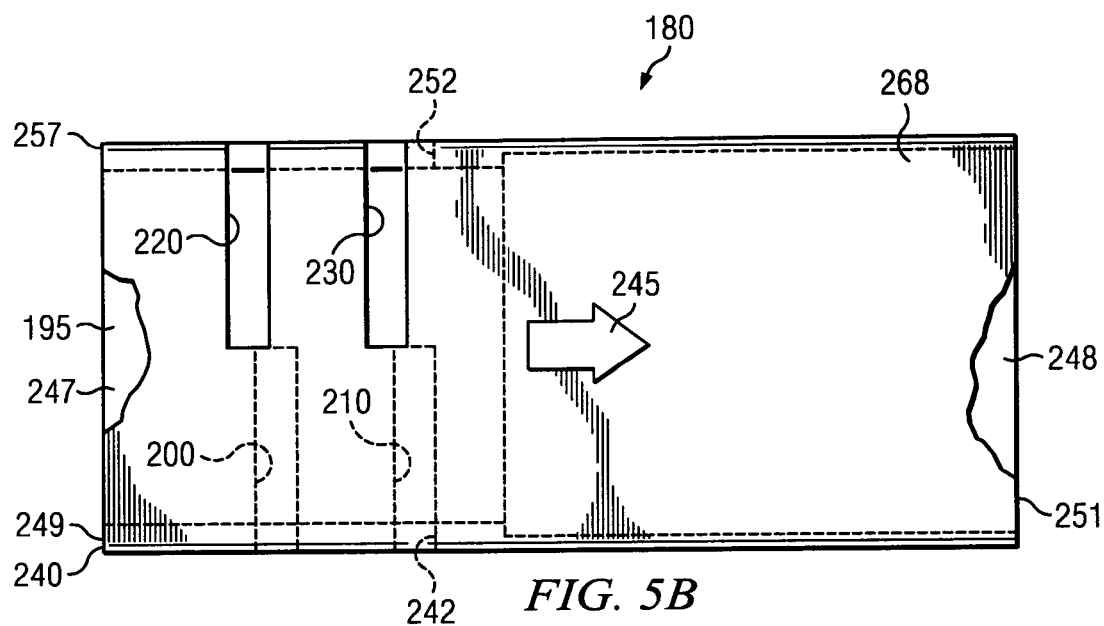
FIG. 5b is a plan view of a gate of a preferred embodiment of the invention.
Figure 5C:
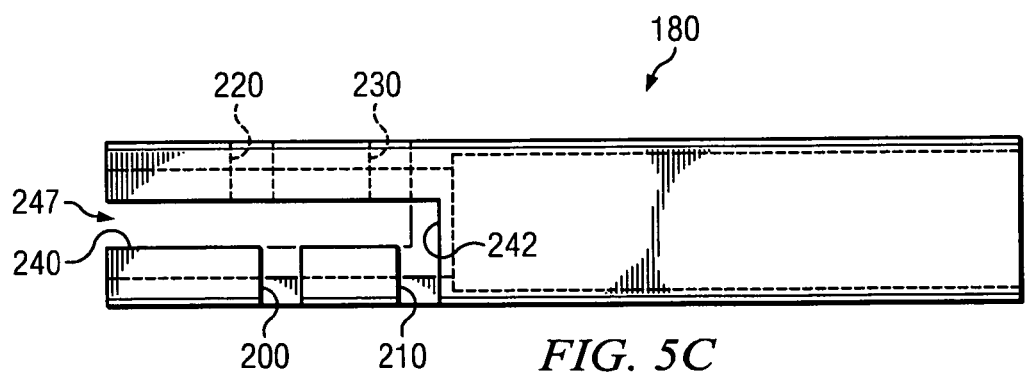
FIG. 5c is an elevated view of a gate of a preferred embodiment of the invention.

FIGS. 5*a*, 5*b* and 5*c* illustrate an embodiment of gate 180. Gate 180 has a gate body 223 bordered by side wall 271, bottom side 269, side wall 284 and top side 268. The gate body also includes saw end 249 and distractor end 251. In the preferred embodiment, gate 180 has a length of between about 5 cm and about 10 cm, a width of between about 2.2 cm and 5.8 cm and a height of between about 0.7 cm and about 2.9 cm.

Gate 180 is provided with saw guide 220 and saw guide 230. Saw guides 220 and 230 are a pair of slots which are situated approximately the center of top side 268 to the center of side wall 284, encompassing approximately ¼ of the perimeter of gate body 223. The pair of saw guides are in parallel planes. Saw guide 220 and saw guide 230 terminate in handle guide 257. Handle guide 257 forms a slot generally in the center of side wall 284. Handle guide 257 is provided with handle stop 252. The width of saw guides 220 and 230 and handle guide 257 in the preferred embodiment is between about 0.5 cm and 1.5 cm.

Gate body 223 is also provided with saw guide 200 and saw guide 210. Saw guides 200 and 210 are a matched pair of slots which are situated approximately the center of bottom side 269 to the center of side wall 271, encompassing approximately ¼ of the perimeter of gate body 223. The pair of saw guides are in parallel planes. Saw guide 200 and saw guide 210 terminate in handle guide 240. Handle guide 240 forms a slot generally in the center of side wall 271. Handle guide 240 is provided with handle stop 242. The width of saw guide 200, saw guide 210 and handle guide 240 in preferred embodiment is between about 0.5 cm and about 1.5 cm.

Saw guide 220, saw guide 230 and handle guide 257 are ductedly connected. Saw guide 220 and saw guide 230 are on centers of between about 0.5 cm to 3.5 cm in the preferred embodiment. Further, saw guide 220 is approximately 0.9 cm from saw end 249.

Saw guide 210, saw guide 200 and handle guide 240 are ductedly connected. Saw guide 210 and saw guide 200 are on centers of between about 0.5 cm to 3.5 cm in the preferred embodiment. Further, saw guide 210 is approximately 1.9 cm from saw end 249.

Gate body 223 is further provided with interior channel 195 which is longitudinally centered within gate body 223. Interior channel 195 includes saw entrance 247. Saw entrance 247 in the preferred embodiment has dimensions slightly larger than guide body 310 which will be described in more detail with respect to FIG. 6. The diameter of saw entrance 247 is maintained by interior channel 195 from saw entrance 247 until gate lip 185. At gate lip 185, interior channel 195 increases in height and width to accommodate the exterior of distractor 110. The dimensions of interior channel 195 remain constant from gate lip 185 to distractor end 251 terminating in distractor entrance 248.

In one embodiment, gate 180 can also include raised indicator arrow 245 or other visual aid or tactile indicator to indicate which end of gate 180 is to be inserted over distractor 110.

In the preferred embodiment, many gates are provided in a kit during surgery. The gates each have saw guides that are spaced apart at different lengths with respect to the top and the bottom of each gate. The different spacings correspond to different distances that the vertebrae have slipped. In one preferred embodiment, in the less severe cases, saw guides 230 and 220 will be offset from saw guides 200 and 210 by about 1 mm. The offset between saw guides 230 and 220 and saw guides 200 and 210 will increase by 2 mm increments. In more severe cases, the amount of slip will be more pronounced and the offset can be approximately 20 mm. Position of saw guides 200 and 210 on gate 180 will stay constant. The gates also vary in height to match the variable height of the distractor.

Figure 7A:
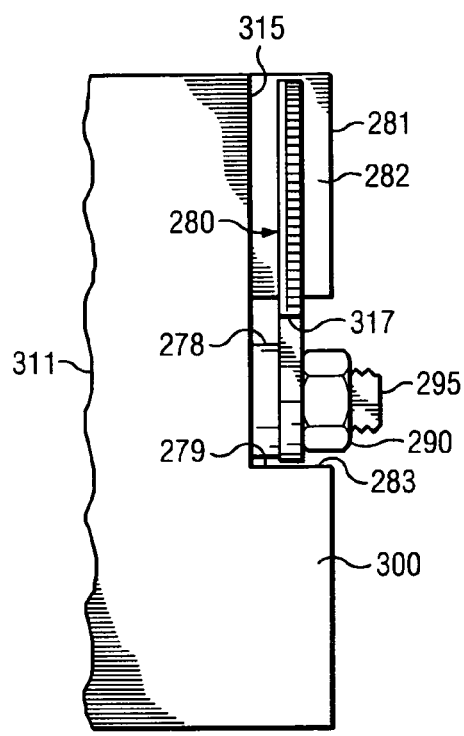
FIG. 7a is a partial plan view of the relational section of the saw of a preferred embodiment of the invention.
Figure 7B:
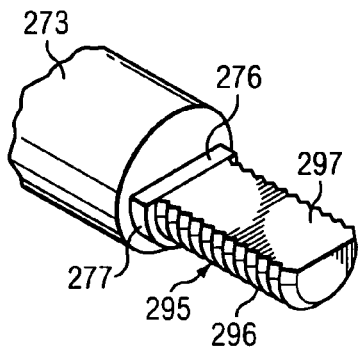
FIG. 7b is a partial isometric view of the spindle shaft of a preferred embodiment of the invention.
Figure 7C:
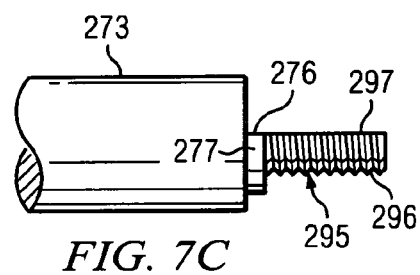
FIG. 7c is a partial side view of the spindle shaft of a preferred embodiment of the invention.

Referring now to FIGS. 6 and 7*a*, an embodiment of saw 250 can be seen. Saw 250 includes saw handle 260 to conical section 262. Conical section 262 is connected to handle post 265. Handle post 265 integrally supports saw guide post 270. Saw guide post 270 is perpendicular to the longitudinal axis of saw 250. Handle post 265 includes abutment surface 272 narrows to the diameter of spindle shaft 273. Abutment surface 272 connects spindle shaft 273 with blade seating shoulder 275. Blade seating shoulder 275 is flat surface 276 and semicircular section 277. Blade seating shoulder 275 is connected to bolt 295. Bolt 295 has threaded section 296 which is directly adjacent to flat surface 276 and semicircular section 277. Bolt 295 has a threaded section 296 and a flat surface 297.

Saw 250 includes guide body 310. Guide body 310 includes a rectangular section 311 and an angular section 312. Rectangular section 311 in the preferred embodiment is sized to fit within saw entrance 247 as shown in FIG. 5*b* and distractor channel 115 shown in FIG. 2. The rectangular section tolerance must be such that rectangular section 311 slides longitudinally with respect to distractor channel 115 and interior channel 195 without significant angular play about the longitudinal axis. In the preferred embodiment, these tolerances are approximately 0.3 mm. Angular section 312 connects to flat surface 313. Guide body 310 also includes spindle hole 301 which traverses the longitudinal axis of guide body 310 and is sized to fit around spindle shaft 273. Spindle hole 301 is sized to allow rotation with respect to spindle shaft 273.

Rectangular section 311 includes spacer 300, saw alignment stop 281 and saw alignment stop 279. As can be seen best in FIG. 7*a* and FIG. 6, saw alignment stop 281 includes a horizontal surface 282. Saw alignment stop 279 includes vertical surface 283.

When assembled, saw 250 provides for 90 degrees rotation of saw handle 260 with respect to guide body 310. Thrust bearing 302 rests adjacent abutment surface 272. Guide body 310 rests on spindle shaft 273 via spindle hole 301. Flat surface 313 is adjacent angular section 312 and thrust bearing 302 providing a bearing surface between abutment surface 272 and flat surface 313. Thrust bearing 278 resides around semicircular section 277 of blade seating shoulder 275 adjacent vertical end 315 of rectangular section 311. Locking hole 285 of saw blade 280 is adjacent flat surface 276 and semicircular section 277 of blade seating shoulder 275. Locking hole 285 includes flat surface 316 which when brought into contact with flat surface 276, prevents rotation of saw blade 280 with respect to blade seating shoulder 275, consequently, with respect to saw handle 260. Lock nut 290 is threaded onto threaded section 296 of bolt 295. Flat surface 276, flat surface 316 and saw alignment stop 281 are parallel with the axis of saw guide post 270.

Saw 250 and all its components are made from titanium, stainless steel, or other material which is used with surgical tools and equipment. In the preferred embodiment, rectangular section 311 of saw 250 is provided in several sizes in a set of several sizes to match the sizes of the distractor 110, as previously described. Alternatively, a set of several saws 250 is provided, each having a rectangular section 311 whose cross-section is sized to match the distractor channel 115 of the set of distractors 110. In addition, a set of blades may be provided each having different dimensions to achieve different lumbar dimensions.

Figure 8A:
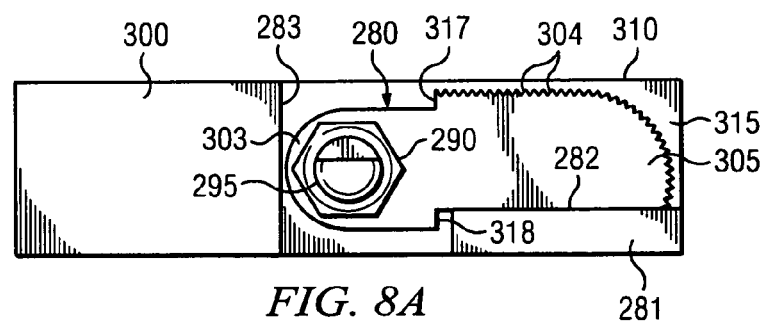
FIG. 8a is an end view of the saw with the saw blade in a lowered position of a preferred embodiment of the invention.
Figure 8B:
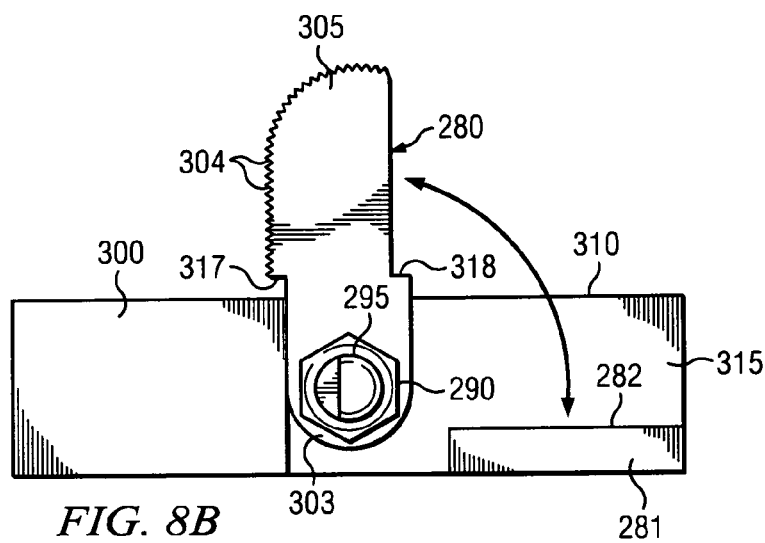
FIG. 8b is an end view of the saw with the saw blade in a raised position of a preferred embodiment of the invention.

FIGS. 8a and 8b are end views of saw 250. FIG. 8a illustrates saw blade 280 in lowered position. In lowered position, saw blade 280 is flush with guide body 310. FIG. 8b illustrates saw blade 280 in raised position. In raised position, saw blade 280 is perpendicular to guide body 310.

In the preferred embodiment, saw blade 280 is between 0.9 cm and 4.9 cm long with a width of between 1 mm and 5 mm. Saw blade 280 has a flat bottom and two curved ends 303 and 305. Saw blade 280 includes a locking hole 285 of approximate diameter and shape as bolt 295. Curved end 305 includes saw teeth 304 having a height of about 0.5 mm and about 1.5 mm. Saw blade 280 also includes notches 317 and 318. As shown in FIG. 8b, saw blade 280 in its raised position rests adjacent vertical surface 283 which prevents it from rotating counterclockwise. In lowered position, as shown in FIG. 8a, notch 318 rests adjacent horizontal surface 282 and prevents rotation of the saw blade clockwise.

Figure 9:
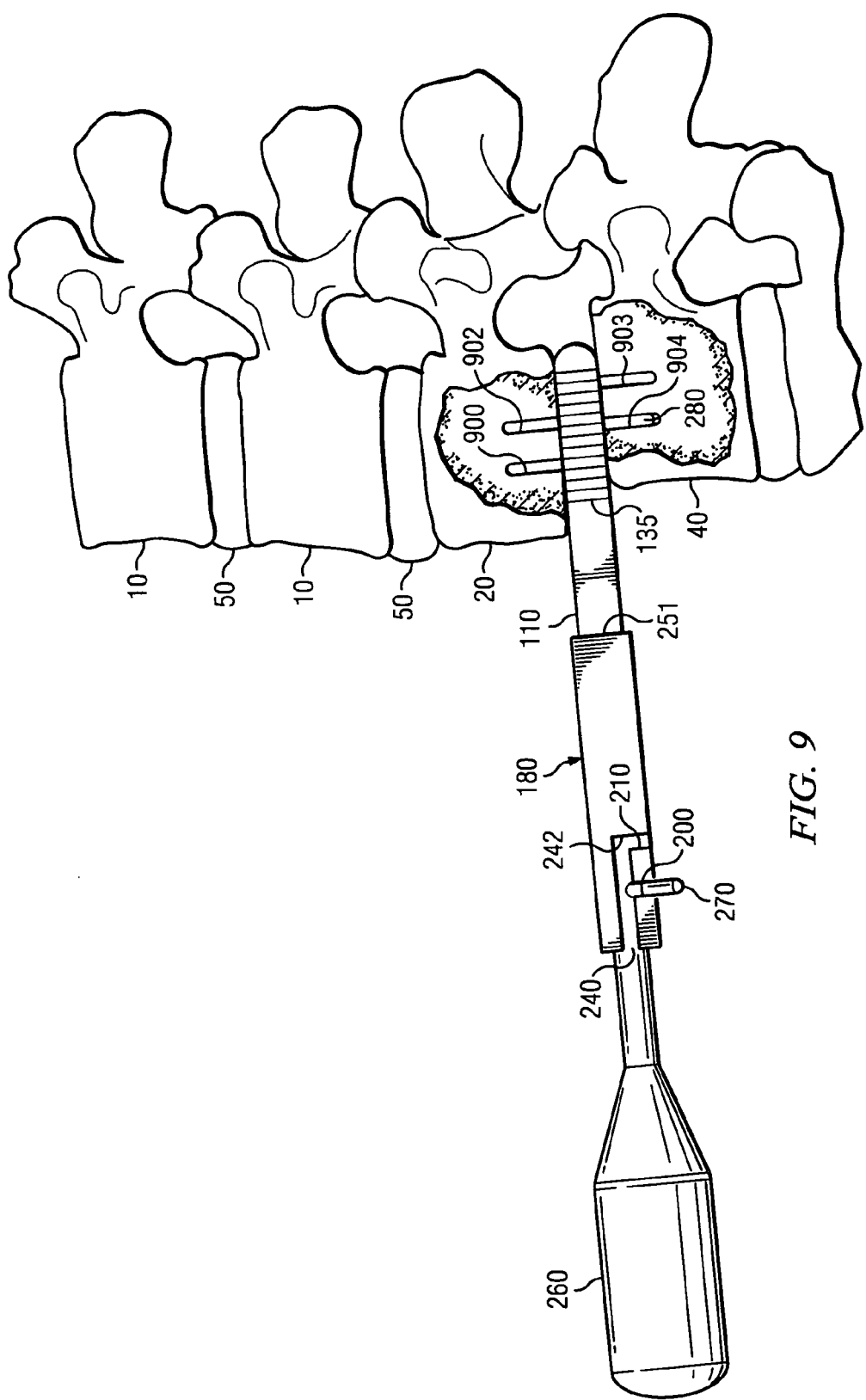
FIG. 9 is a cut away side view of section of a human spine with the distractor, gate, and saw in place between the vertebrae.

Referring now to FIG. 9, in use, gate 180 is placed over the anterior end of distractor 110 and advanced until anterior end 111 rests against gate lip 185. Saw 250 is placed in lowered position. Rectangular section 311 is placed in interior channel 195 and advanced through distractor channel 115 until spacer 300 reaches distractor stop 122 or saw guide post 270 reaches handle stop 242.

In use, the saw is used to make two sets of receiving notches in the upper and lower vertebrae that correspond to the positions of the saw guides. More particularly, saw 250 is retracted until saw guide post 270 is directly adjacent saw guide 230. Saw handle 260 is rotated clockwise 90 degrees such that saw guide post 270 advances through saw guide 230 on gate 180. Rotation of saw handle 260 will rotate saw blade 280 causing it to cut into superior vertebra 20 thereby forming a slot 900. Distractor torque handle 235 is grasped to apply counter torque and prevent rotation of the saw from displacing distractor 110 angularly with respect to the effected vertebrae. Saw handle 260 is then rotated counterclockwise positioning saw guide post 270 in handle guide 257. Saw 250 is then extracted such that saw guide post 270 is adjacent saw guide 220. Saw handle 260 is then rotated clockwise 90 degrees such that saw guide post 270 advances into saw guide 220. Rotation of saw handle 260 rotates saw blade 280 thereby cutting into superior vertebra 20 and forming slot 902. Saw guide post 270 is then rotated counter-clockwise so that saw guide post 270 resides in handle guide 257.

Saw blade 280 is placed in its lowered position. Saw 250 is then removed from distractor channel 115 through interior channel 195. Saw 250 is then rotated 180 degrees about its axis and rectangular section 311 replaced is in interior channel 195 of gate 180. Saw 250 is further reinserted into distractor channel 115.

Saw guide post 270 is adjacent saw guide 210. The saw handle is rotated clockwise 90 degrees such that saw guide post 270 enters saw guide 210. Rotation of saw handle 260 consequently rotates saw blade 280 exposing saw teeth 304 to inferior vertebra 40 thereby cutting into inferior vertebrae 40 thereby forming slot 903. Distractor torque handle 235 is used to apply counter torque and prevent the saw rotation from displacing distractor 110. Saw handle 260 is then rotated clockwise such that saw guide post 270 advances through the saw guide and into handle guide 240. Saw 250 is then extracted such that saw guide post 270 advances through handle guide 240 until it is adjacent saw guide 200. Saw handle 260 is then rotated 90 degrees such that saw guide post 270 advances into saw guide 200. The rotation of saw handle 260 rotates saw blade 280 causing a second cut into inferior vertebra 40 thereby forming slot 904.

Saw 250 is removed through distractor channel 115 and interior channel 195. Gate 180 is then removed from the anterior end of distractor 110.

Slots 900, 902, 903 and 904 in superior vertebra 20 and inferior vertebra 40 are substantially consistent with the spacing on gate 180 between saw guides 200, 210, 220, and 230, respectively.

The novel implant is then prepared to be inserted.

Figure 11:
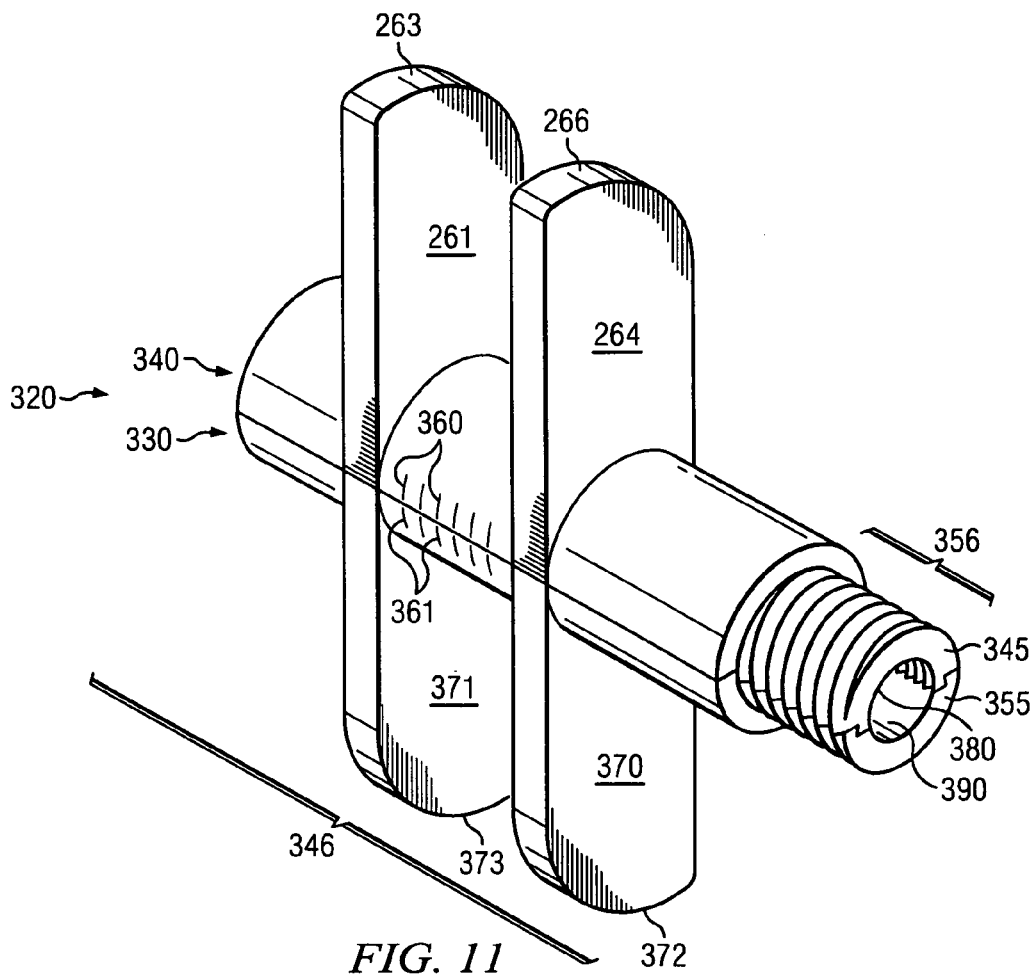
FIG. 11 is an isometric view of the implant of a preferred embodiment of the invention.
Figure 10:
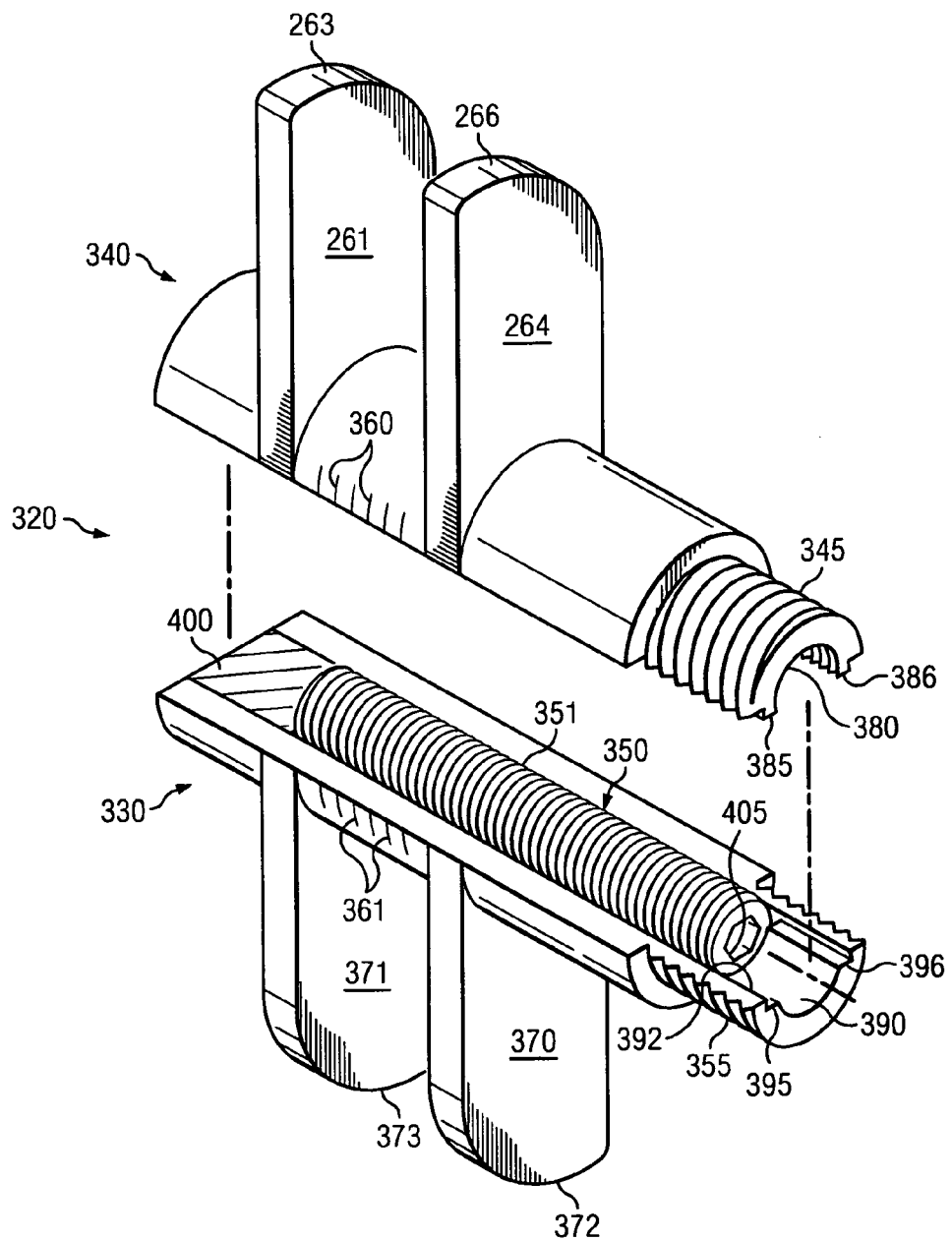
FIG. 10 is an exploded isometric view of the implant of a preferred embodiment of the invention.
Figure 12:
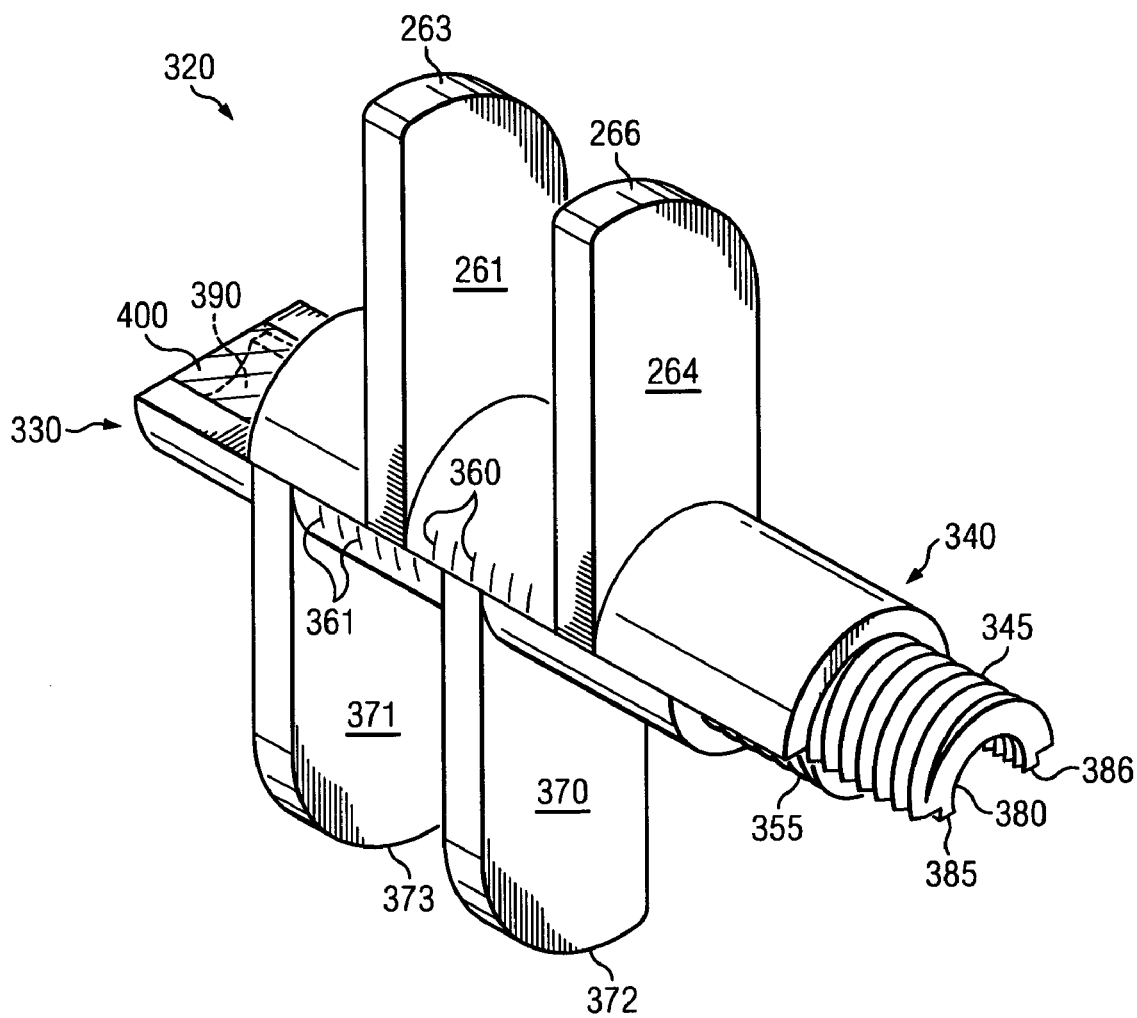
FIG. 12 is an isometric view of the implant in an extended position of a preferred embodiment of the invention.

Referring to FIGS. 10, 11 and 12, implant 320 is described. Implant 320 is comprised of two semi-cylindrical halves, upper half 340 and lower half 330. Lower half 330 includes parallel radially exposed and planar radial anchors 264 and 261. The radial anchors are integrally formed with upper half 340. Radial anchor 264 further includes curved surface 266. Radial anchor 261 includes curved surface 263.

Lower half 330 includes two parallel planar radial anchors 370 and 371. Radial anchors 370 and 371 are integrally formed with lower half 330. Radial anchor 370 includes curved surface 372. Radial anchor 371 includes curved surface 373.

Upper half 340 includes upper threaded collar 345. Lower half 330 includes lower threaded collar 355. The exterior of the upper half includes index marks 360. Index marks 360 correspond with index marks 361 on lower half 330.

Upper half 340 includes upper channel 380 which is threaded. Lower half 330 includes lower channel 390. Lower channel 390 is not threaded. Upper half 340 is joined to lower half 330 with a mating interconnection between dovetail guide 386 and dovetail guide 385 found on upper half 340 and dovetail slot 396 and dovetail slot 395, respectively, located on lower half 330.

Lower half 330 includes set screw stop 400 integrally formed with lower half 330 and residing within lower channel 390. Set screw stop 400 is solid plug which fills lower channel 390 beyond end of set screw 350.

Lower half 330 includes set screw step 392. Set screw step 392 extends into upper channel 380 and in upper half 340 and lower channel 390 in lower half 330. Set screw step 392 decreases diameter of upper channel 380 and lower channel 390 by approximately 2 mm.

As can best be seen in FIG. 12, when assembled, upper half 340 and lower half 330 of implant 320 are engaged in a sliding relationship provided by the dovetail guides 385 and 386 residing in dovetail slots 395 and 396. As can be seen in FIG. 11, when assembled, upper half 340 and lower half 330 form implant body 346. Radial anchor 264 is aligned with radial anchor 370. Radial anchor 261 is aligned with radial anchor 371. Furthermore, upper threaded collar 345 and lower threaded collar 355 are aligned and form a cylindrical threaded attachment collar 356.

In use, set screw 350 can be rotated either counter-clockwise or clockwise within lower channel 390 and upper channel 380. The set screw is retained in position by set screw stop 400 and set screw step 392. As set screw 350 is rotated, threads 351 engage the threads on upper channel 380 and slide upper half 340 with respect to lower half 330. As upper half 340 and lower half 330 are displaced, radial anchors 264 and 261 are displaced with respect to radial anchors 370 and 371 along the longitudinal axis of implant 320.

Implant 320 in the preferred embodiment is made from titanium, stainless steel, alloys such as titanium allow, or other materials which are easily sterilizable. Implant 320 or parts thereof, may also be made from composite materials such as synthetic bone. Some composites or synthetic bone products include demineralized bone matrix, collagen, ceramics, cements, and polymers, such as silicone and some acrylics and include products such as Vitoss, Cortoss, Rhakoss, Pro Osteon, and Gu-Bang.

In the preferred embodiment, implant body 346 is between about 0.5 cm to about 2.5 cm in diameter and between about 2.0 cm and about 4.5 cm in length. In the preferred embodiment, cylindrical threaded attachment collar 356 is between about 0.4 to about 2.4 cm in diameter and between about 0.5 and 2.0 cm in length. In the preferred embodiment, radial anchors 264, 261, 370 and 371 have a height (as measured from the center plane of the implant) of between about 0.5 cm and about 3.5 cm with an aspect ratio of ½ to 1½ between radial anchors 264, 261, 370, and 371 and diameter of implant body 346.

In the preferred embodiment, upper half 340 includes exactly two radial anchors and lower half 330 includes exactly two radial anchors. However, in other embodiments, the upper half and lower half of the implant may include more or less than two radial anchors. Furthermore, the upper half and lower half of implant 320 do not necessarily need to include the same number of radial anchors. In embodiments which include different numbers of radial anchors, it will be understood by those skilled in the art that the same number of saw guides must be included on gate 180 in order to correspond with the number and orientation of the radial anchors.

Figure 13A:
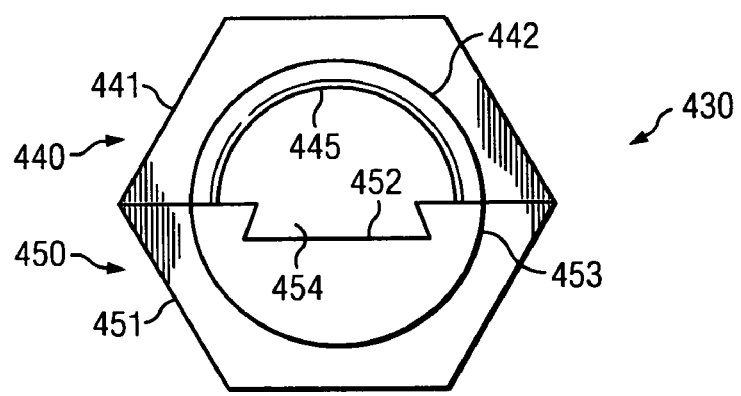
FIG. 13a is an end view of the inserter of a preferred embodiment of the invention.
Figure 13B:
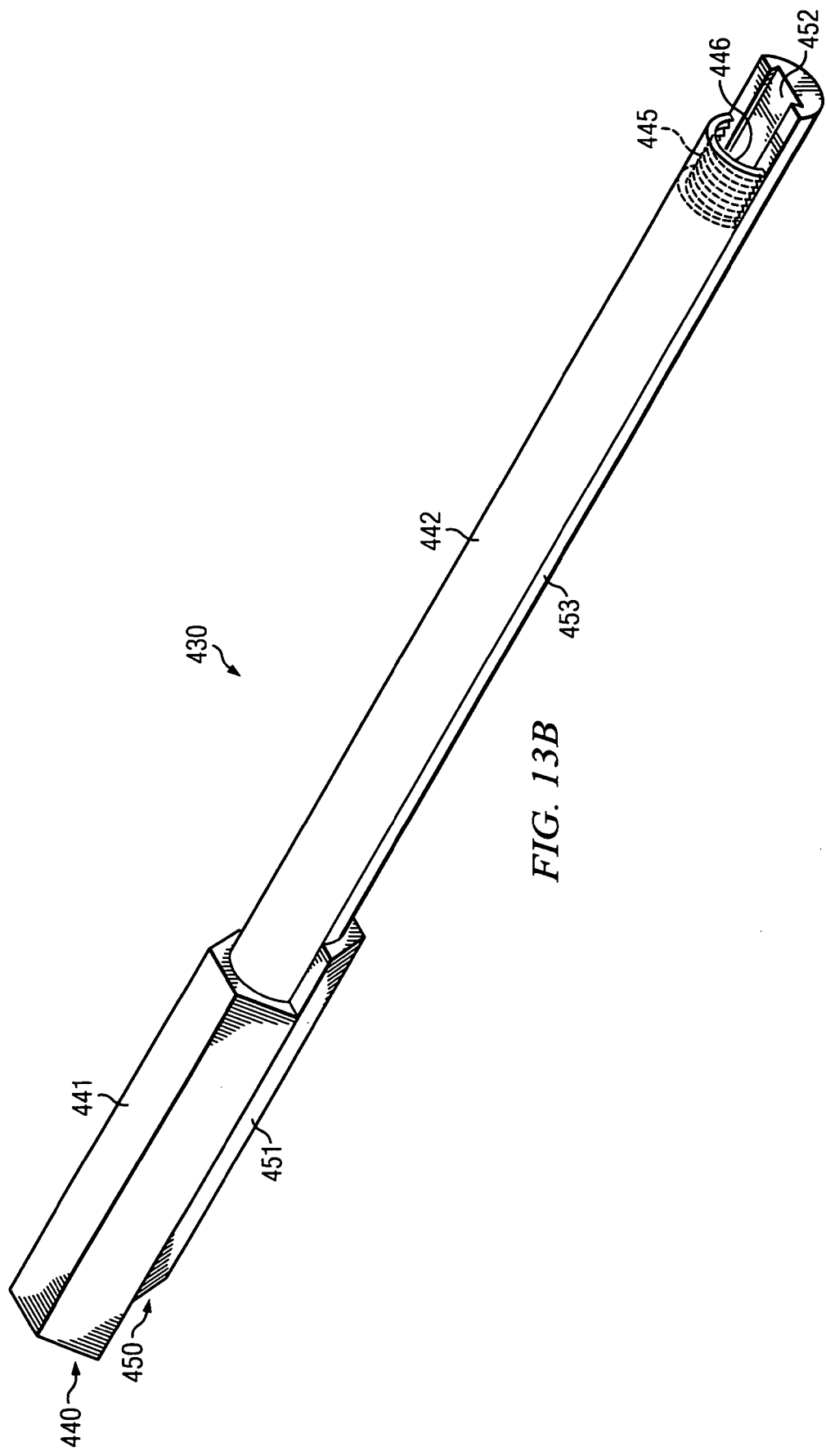
FIG. 13b is an isometric view of the inserter of a preferred embodiment of the invention.

FIGS. 13a and 13b illustrate inserter 430. Inserter 430 includes upper half 440 and lower half 450. Upper half 440 includes upper hexagonal section 441 and upper cylindrical section 442. Within upper cylindrical section 442 resides upper dovetail guide 454. Adjacent upper dovetail guide 454 is implant channel 446. Implant channel 446 includes locking thread 445.

Lower half 450 includes lower hexagonal section 451 and lower cylindrical section 453. Lower cylindrical section 453 includes lower dovetail channel 452. Upper dovetail guide 454 fits within lower dovetail channel 452 and allows for sliding movement between upper half 440 and lower half 450. As can best be seen in FIG. 13b, when upper half 440 and lower half 450 are assembled, inserter 430 assumes an outer circular perimeter. In the preferred embodiment, this outer circular perimeter is sized to fit within distractor channel 115, shown in FIG. 2, with sufficient clearance to allow for rotation of inserter 430. Further, in the preferred embodiment, the hexagonal shape of upper half 440 and lower half 450 and inserter 430 is sized to allow for rotation with a tool such as a spanner wrench. In the preferred embodiment, the length of inserter 430 is sufficient to span the length of distractor body 99.

Locking thread 445 is sized to mate with upper threaded collar 345 on implant 320 as shown in FIGS. 10, 11 and 12.

Figure 15:
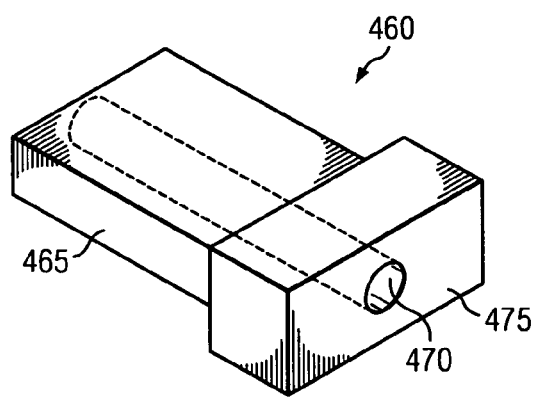
FIG. 15 is an isometric view of a guide block of a preferred embodiment of the invention.

Referring to FIG. 15, guide block 460 will be described. Guide block 460 includes guide block bottom 465 and guide block top 475. Guide block 460 also includes guide hole 470 which is centrally located within the guide block and spans its length. Guide block bottom 465 is sized to fit within distractor channel 115. Guide block top 475 is sized so that it will not fit within distractor channel 115 but rather abut anterior end 111 of distractor body 99 (as shown in FIG. 2).

In use, inserter 430 is used to place the implant in position between the affected vertebra and rotated into position. More particularly then to implant the implant, the amount of offset calculated according to the radiograph is reduced to a number of millimeters. The implant is adjusted using upper adjustment index marks 360 and lower adjustment index marks 361 to an offset position using set screw 350. The amount of offset can be observed by observing the offset between index marks 360 and 361. In an alternate embodiment, the offset can be derived by calculating the number of rotations of the set screw and multiplying by the pitch of the threads. In an alternate embodiment, the pitch of the threads is set to a convenient number so that a single rotation of the set screw results in a predetermined movement of the upper and lower halves, such as 1 mm for example. An example of an offset position is shown in FIG. 12.

In use, inserter 430 is assembled and its cylindrical section is guided into and through guide hole 470 until guide block top 475 reaches the hexagonal section of the inserter.

Figure 14:
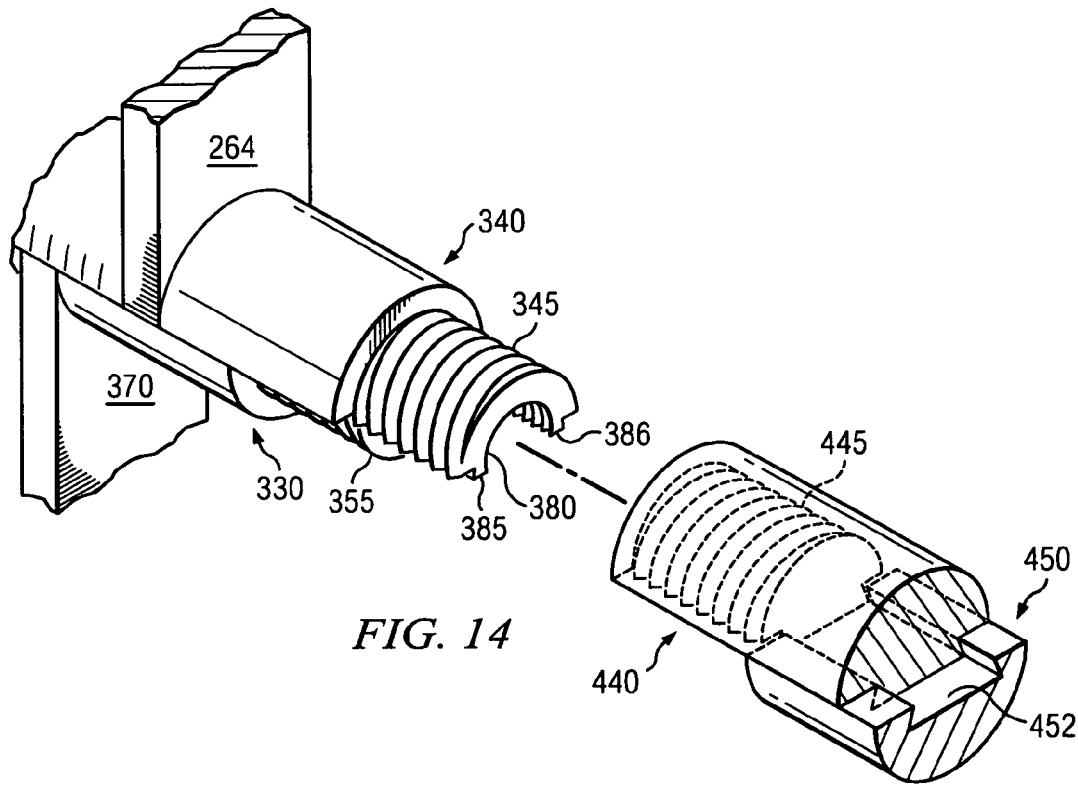
FIG. 14 is a partial isometric view of the inserter and the implant of a preferred embodiment of the invention prior to attachment.

Implant 320 is then connected to inserter 430 as shown in FIG. 14. Locking thread 445 of inserter 430 is engaged with upper threaded collar 345 of implant 320. Inserter lower half 450 is advanced towards implant 320 whereby dovetail guides 386 and 385 of implant 320 are engaged by lower dovetail channel 452 on inserter 430 thereby securing implant 320 to inserter 430.

Figure 16:
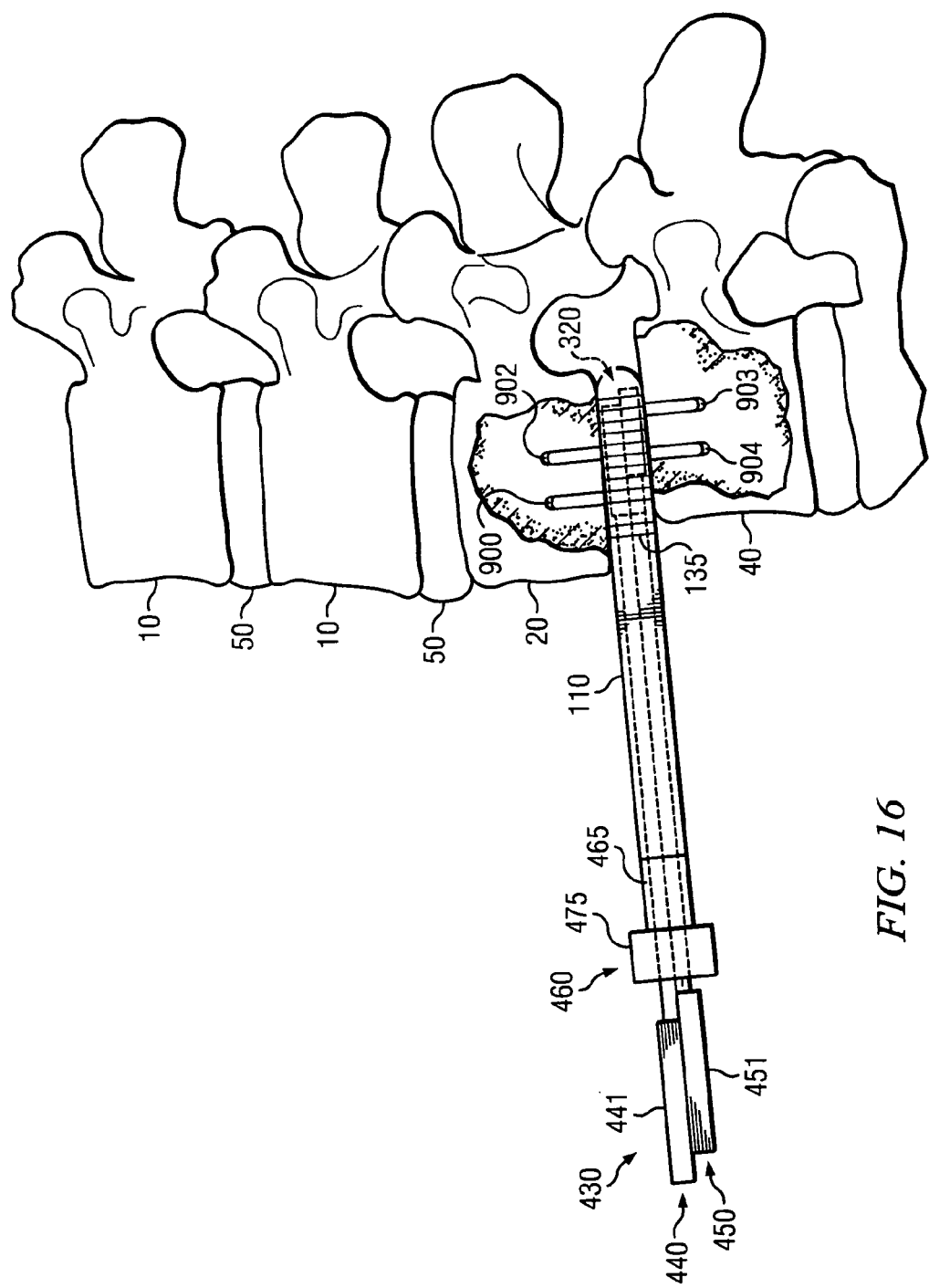
FIG. 16 is a cut away side view of a section of a human spine and an implant during positioning by an inserter of a preferred embodiment of the invention.

Referring now to FIG. 16, the process of inserting implant 320 into the affected vertebra will be described. As previously described, distractor 110 is in position between superior vertebra 20 and inferior vertebra 40. Implant 320, while attached to inserter 430 is oriented and placed within distractor channel 115. Implant 320 is placed in distractor channel 115 with radial anchors 264 and 261, 370 and 371 positioned so that clockwise rotation of the implant will result in radial anchor 264 and 261 encountering superior vertebra 20 and radial anchor 370 and 371 encounter inferior vertebra 40. Using the hexagonal section of inserter 430, implant 320 is advanced within distractor channel 115 a sufficient distance to allow guide block bottom 465 to be inserted into distractor channel 115. Guide block bottom 465 is advanced within distractor channel 115 until guide block top abuts anterior end 111 of distractor body 99.

Implant 320 is then advanced within distractor channel 115 until the hexagonal section of inserter 430 abuts guide block top 475.

The dimensions of guide block top 475 and cylindrical section of inserter 430 are such that when the hexagonal section of the inserter abuts guide block top 475, implant 320 is in proper position in relation to slots 900, 902, 903 and 904 such that radial anchor 264 is adjacent slot 900, radial anchor 261 is adjacent slot 902, radial anchor 370 is adjacent slot 904 and radial anchor 371 is adjacent slot 903.

Inserter 430 is then rotated 90 degrees clockwise such that the radial anchors are rotated into position in the slots in their respective vertebrae.

Once in position, implant 320 is released from inserter 430. The diameter of inserter guide hole 470 should provide sufficient clearance for rotation and transition of cylindrical portion of inserter 430 without excessive play. In the preferred embodiment, the diameter of guide hole 470 should not exceed the diameter of the cylindrical section of inserter 430 by more than 0.1 mm.

To release implant 320 from inserter 430, inserter lower half 450 is retracted anteriorly past superior locking thread 445 and disengages from lower dovetail channel on lower cylindrical section 453 of the inserter. Inserter 430 is rotated 180 degrees such that upper threaded collar 345 is disengaged from locking thread 445 on implant channel 446 on the inserter. Inserter 430 and guide block 460 are then removed from distractor 110.

Distractor 110 is then removed from between superior vertebra 20 and inferior vertebra 40 by pulling anteriorly.

Figure 17:
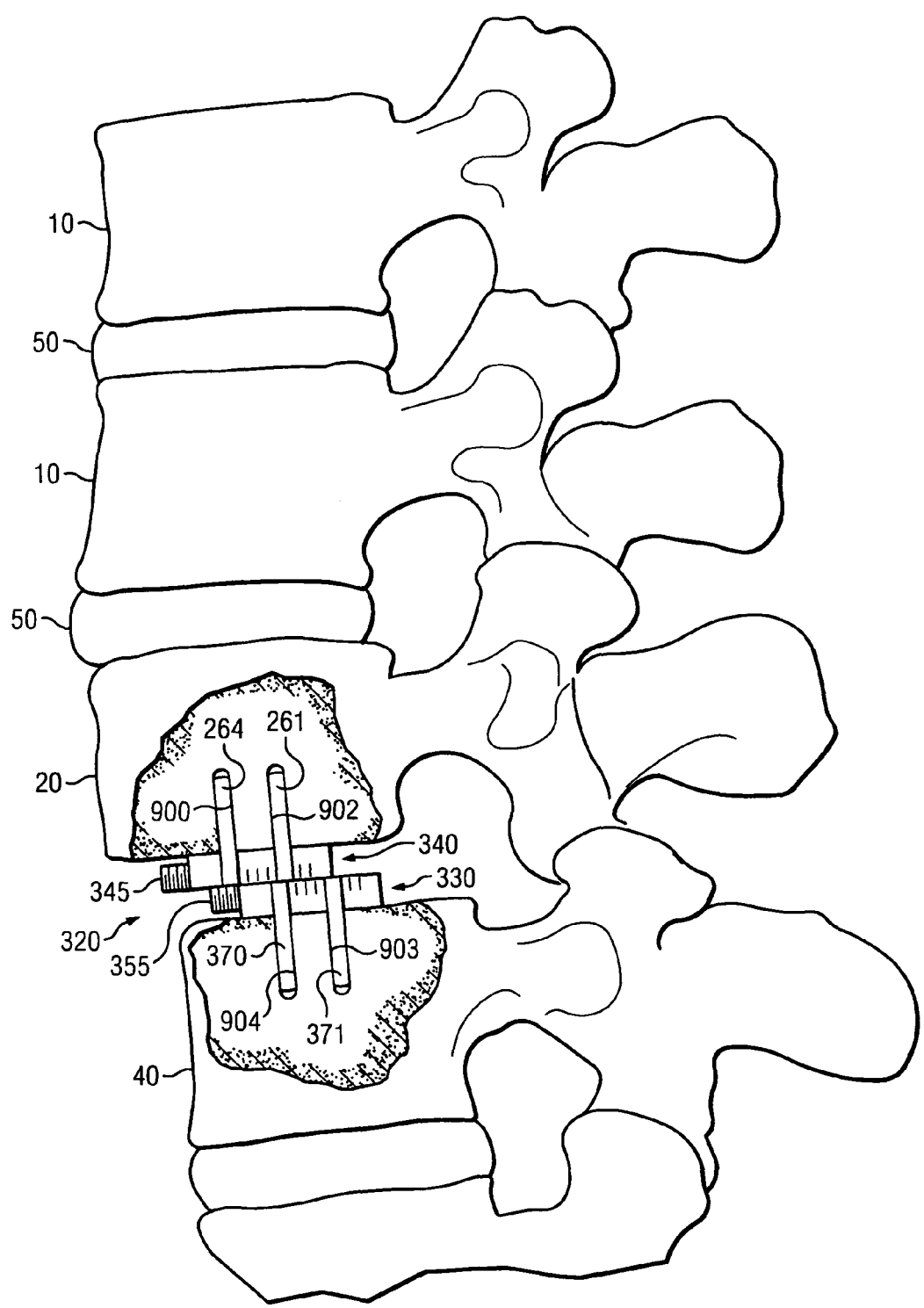
FIG. 17 is a cut away side view of a section of a human spine and an implant in place prior to the alignment of the vertebrae.

FIG. 17 illustrates the positioning of implant 320 between superior vertebra 20 and inferior vertebra 40 after distractor 110 has been removed. Upper half 340 is adjacent superior vertebra 20, radial anchor 264 is located in slot 900, radial anchor 261 is located in slot 902. Lower half 330 is adjacent inferior vertebra 40 and radial anchor 370 is located in slot 904. Radial anchor 371 is located in slot 903.

In order to align superior vertebra 20 and inferior vertebra 40, upper half 340 and lower half 330 are aligned. A spanner is inserted into spanner slot 405 of implant 320. Set screw 350 is rotated to move lower implant half 330 anteriorly and upper implant half 340 posteriorly. In one embodiment, for each complete 360 degrees turn of the set screw will move lower half 330 1 mm with respect to upper when alignment of the implant halves is complete, the threads in upper threaded collar 345 and in lower threaded collar 355 will align. Ideally, alignment of the implant halves will align the vertebrae.

After alignment of the vertebrae, an interbody arthrodesis is performed on each side of implant 320 and between remaining distended disk 70. The technique for interbody arthrodesis is surgeon's choice from those known techniques.

Figure 19A:
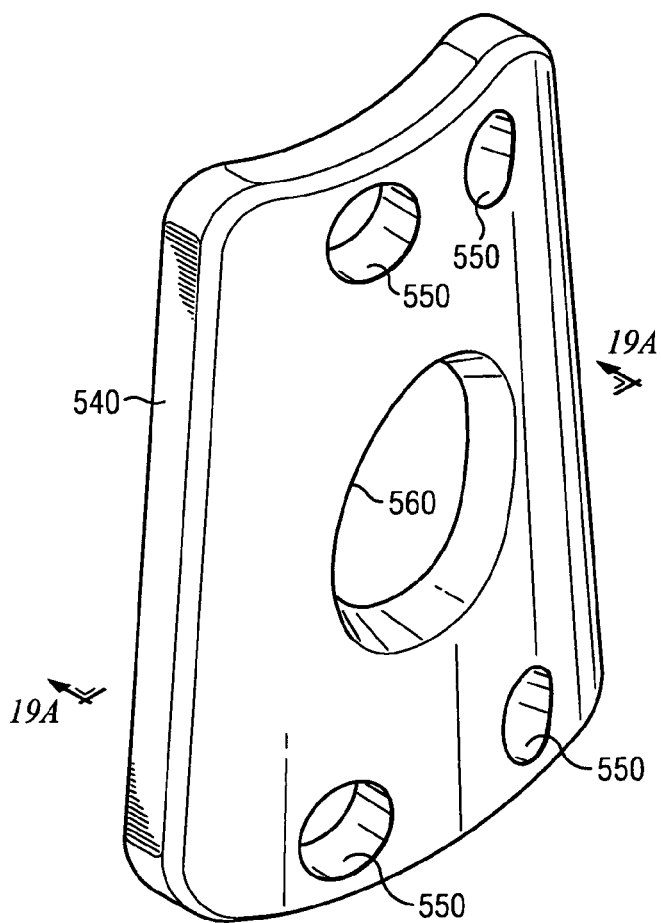
FIG. 19a is an isometric view of a plate of a preferred embodiment of the invention.
Figure 19B:
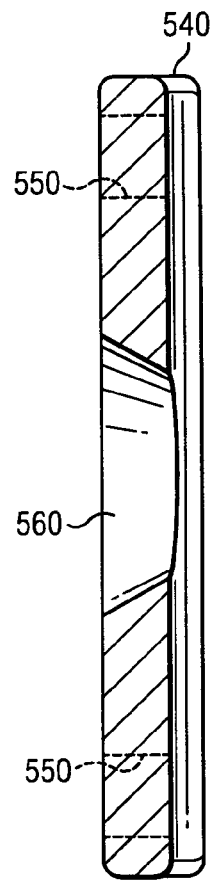
FIG. 19b is a cut away side of a plate of a preferred embodiment of the invention.

FIGS. 19*a* and 19*b* illustrates one embodiment of plate 540. Plate 540 is selected based on shape and size of individual patient's vertebrae. In one embodiment, the height of plate 540 is between 2.5 cm and 7 cm and the width of plate 540 is between 1.5 cm and 5 cm. Depth of plate 540 is between 0.2 cm and 1.5 cm. Plate 540 is slightly concave to approximate the curvature of inferior vertebra 40 and superior vertebra 20.

Plate 540 includes plate nut hole 560 in its approximate center. The diameter of plate nut hole 560 on the anterior side of plate 540 is between 0.65 cm and 3.4 cm while the diameter of plate nut hole 560 on the posterior side of plate 540 is between 0.45 cm and 2.5 cm.

Plate 540 also includes four holes 550. Each hole 550 should have diameter between about 1 mm and about 9 mm. But these diameters can vary. The plate is secured to the vertebra by stainless steel screws as known in the art.

Preferably, plate 540 should be made of titanium or stainless steel.

Figure 18:
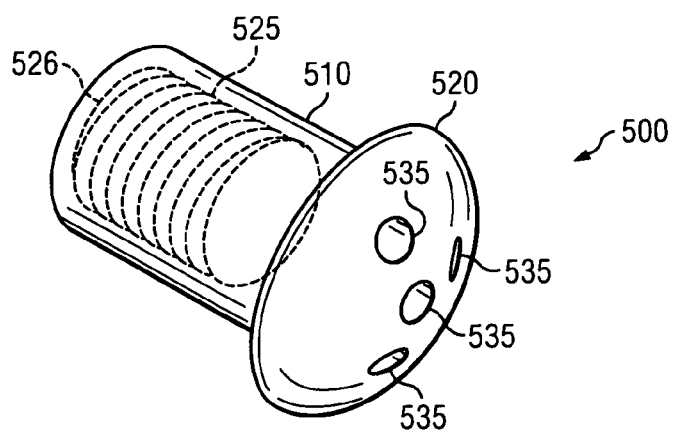
FIG. 18 is an isometric view of a nut of a preferred embodiment of the invention.

FIG. 18 illustrates one embodiment of nut 500. Nut 500 has nut head 520 which is elliptical. Diameter of nut head 520 is between 0.65 cm and 3.4 cm preferably. Nut head 520 contains spanner holes 535. Nut body 510 has diameter of between 0.5 cm and 2.5 cm. The diameter of nut body 510 should be approximately the same as diameter of implant body 346. The length of nut body 510 is between 0.2 cm and 6 cm. Nut 500 should be construction of titanium or stainless steel. Other rigid materials can be used. Nut body 510 includes threaded hole 526. Threaded hole 526 is threaded to match the threads of upper threaded collar 345 and lower threaded collar 355 on implant 320.

Figure 20:
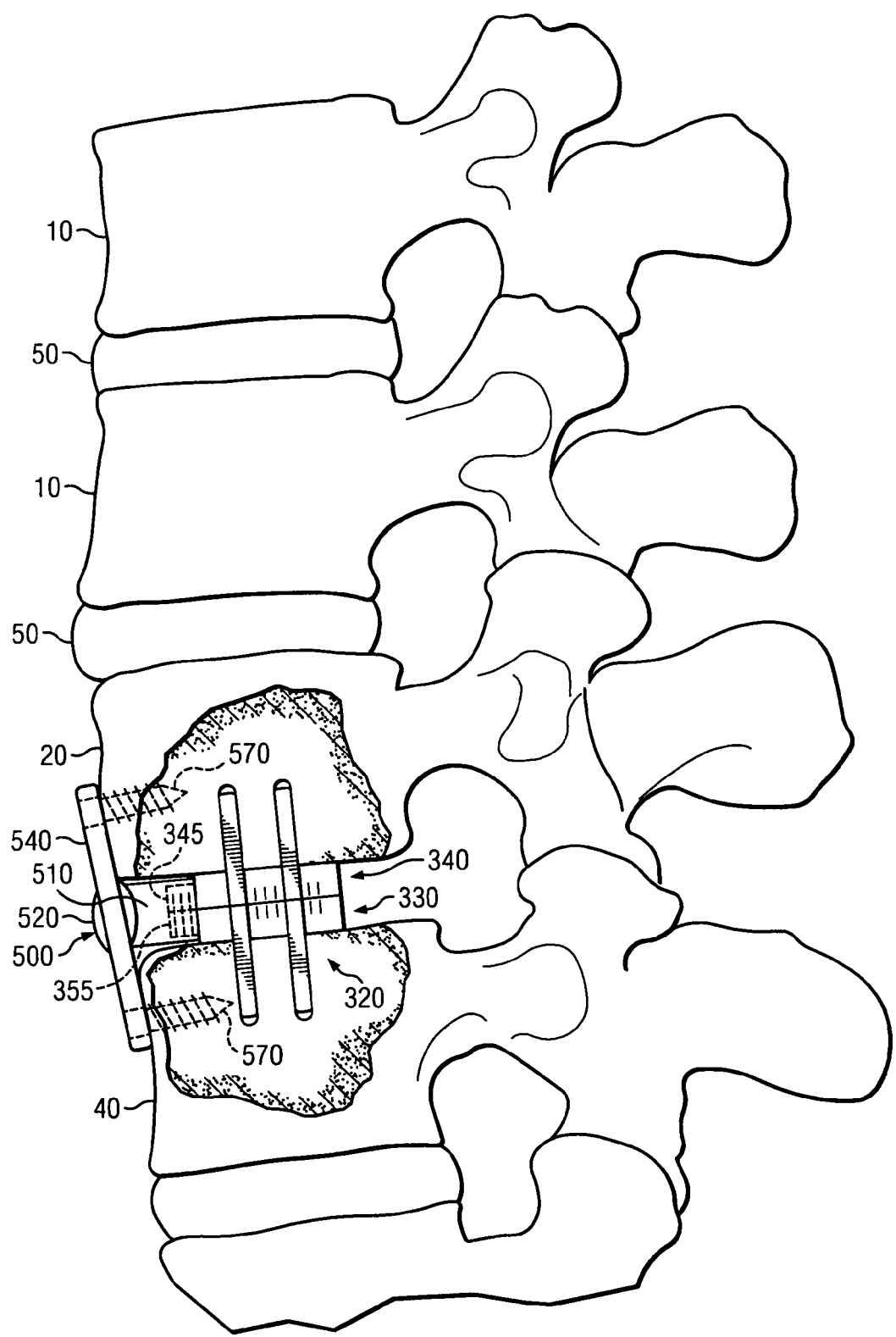
FIG. 20 is a cut away side view of a section of a human spine with an implant in a retracted position and a nut and a bolt in place.

In use, to help secure implant 320 in position, nut 500 and plate 540 are used, as illustrated in FIG. 20. Nut body 510 is placed through plate nut hole 560. Nut thread 525 of threaded hole 526 is then aligned with and threaded onto upper threaded collar 345 and lower threaded collar 355. Nut 500 prevents implant upper half 340 and implant lower half 330 from moving horizontally against each other.

Plate 540 is then properly aligned with the shape of superior vertebra 20 and inferior vertebra 40. Corticocancellous screws 570 are placed into each of the plate screw holes 550 and screwed into the respective vertebrae by traditional techniques within the field. The difference in diameters between plate nut hole 560 from front to back allows articulation of the bolt with respect to the plate. Once plate 540 is attached to superior vertebrae 20 and inferior vertebrae 40 with screws 570, and is secured via nut 500 to implant 320 the device acts as a monolithic structure preventing rotational, lateral or anterior/posterior movement of vertebral bodies 20 and 40 with respect to each other, allowing ossification of said vertebral bodies.

Surgery is completed by standard anterior approach surgery techniques and implant is in place.

In the event that adjustments need to be made to implant 320, screws 570, nut 500 and plate 540 can be removed and set screw 350 adjusted with any appropriate spanner head wrench. Nut 500, plate 540 and screws 570 are then replaced.

Figure 21:
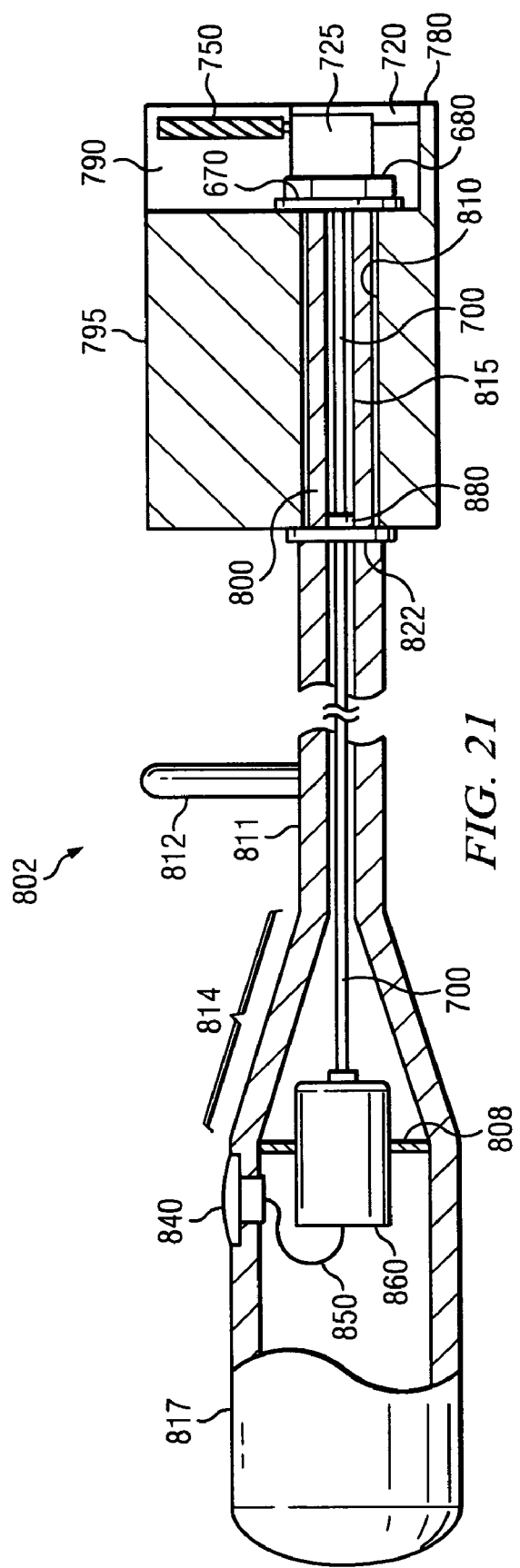
FIG. 21 is a cut away side view of a saw in an alternate saw embodiment.
Figure 22A:
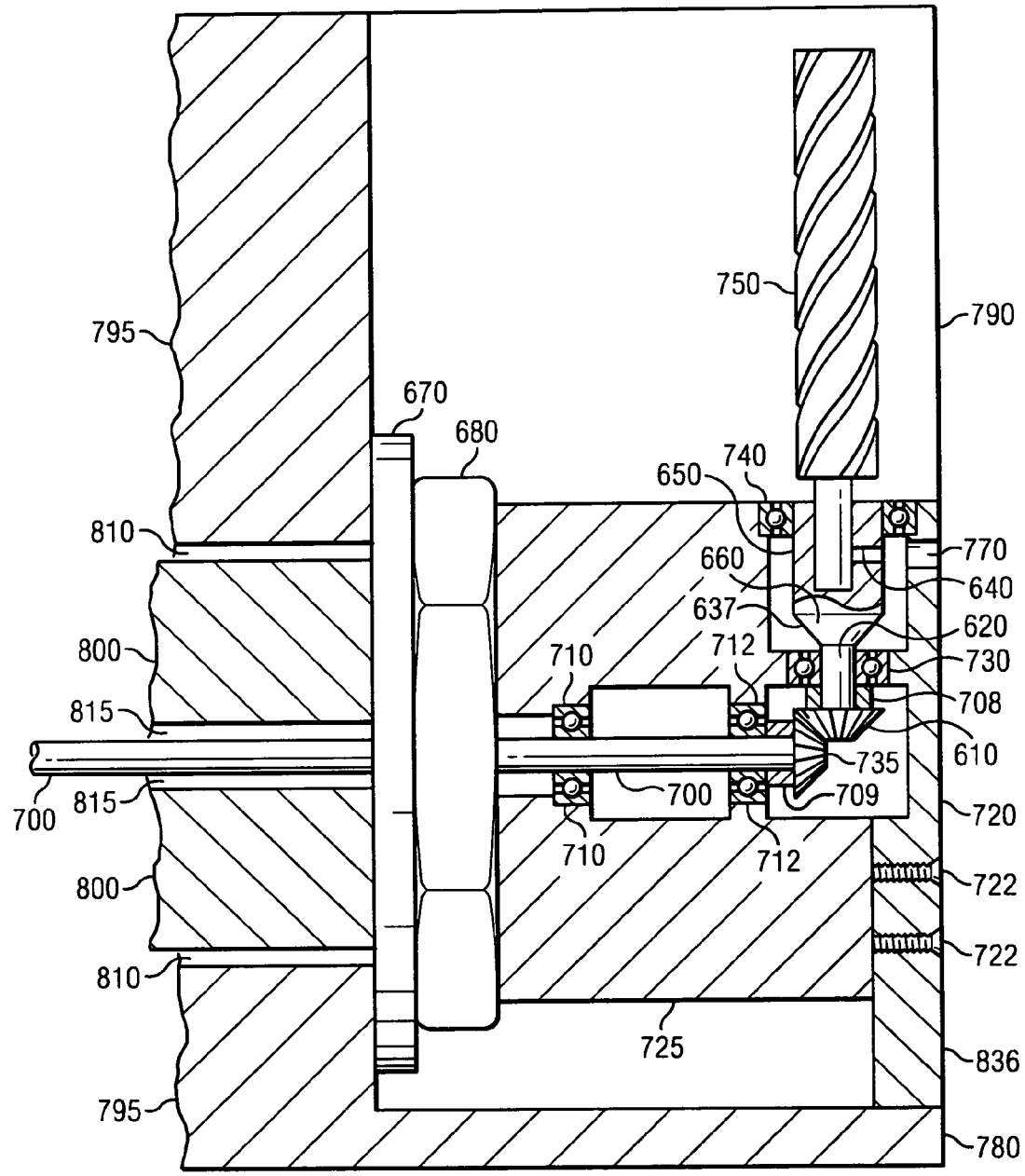
FIG. 22a is a cut away side view of the end of saw in an alternate embodiment of the invention.
Figure 22B:
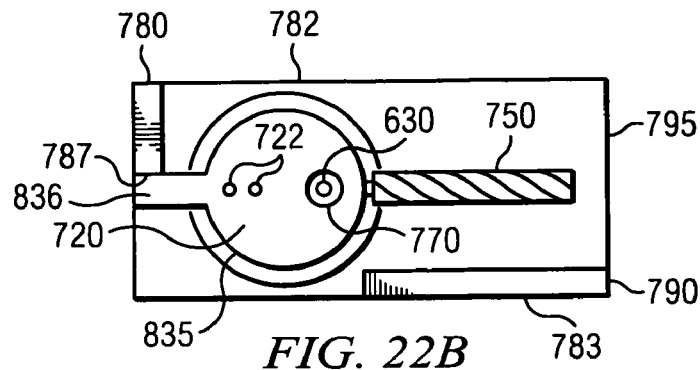
FIG. 22b is an end view of the end of an alternate saw embodiment.

FIGS. 21, 22*a* and 22*b* illustrate another preferred embodiment of the saw. FIG. 21 shows saw 802 with mill bit 750. Saw 802 includes handle 817 and conical section 814. Interior of handle 817 includes motor 860. Motor 860 is attached to mounting frame 808. Motor 860 is connected to transmission shaft 700. Switch 840 is integrated into handle 817 and is connected to motor 860 through wire 850. Switch 840 activates and deactivates motor 860. Motor 860 is connected to power source such as a rechargeable lithium ion battery or another renewable power supply as known in the art Motor 860 rotates transmission shaft 700 between 15,000 to 20,000 rpm. In another preferred embodiment, motor 860 has variable speeds and speed of motor 860 is modulated through use of switch 840.

Conical section 814 is connected to handle post 811. Handle post 811 integrally supports saw guide post 812. Saw guide post 812 is perpendicular to the longitudinal axis of saw 802. Handle post 811 is rigidly attached to spindle shaft 800. Shoulder 822 is positioned between handle post 811 and guide body 795. Guide body 795 is free to rotate with respect to handle post 811 and spindle shaft 800.

Transmission hole 815 extends through handle 817, conical section 814, handle post 811 and spindle shaft 800.

Transmission shaft 700 extends through transmission hole 815. Transmission shaft 700 is kept in position within transmission hole 815 by bushings 880. Transmission shaft 700 extends beyond spindle shaft 800 and into transmission housing 725.

Guide body 795 has spindle hole 810 which transverses the longitudinal axis of guide body 795. Spindle shaft 800 fits within spindle hole 810. Spindle hole 810 allows rotation of spindle shaft 800 about the longitudinal axis of guide body 795. Transmission shaft 700 extends through washer 670 and nut 680 into transmission housing 725.

FIG. 22*a* illustrates the mechanics inside transmission housing 725. Bearings 710 and 712 maintain position of transmission shaft 700 within transmission housing 725 while allowing it to rotate. Transmission shaft 700 terminates in bevel gear 735. Thrust bushing 709 is affixed between bevel gear 735 and bearing 712 and constrains the axial movement of transmission shaft 700. Bevel gear 735 meshes with bevel gear 610 creating 90 degree transmission. Other transmission schemes, such as a flexible cable, will suffice in other embodiments.

Bevel gear 610 is rigidly integrally connected to bearing shaft 620. Bearing shaft 620 is rigidly integrally connected to frustroconical section 637 which is rigidly integrally connected to jaws 650 of chuck 660. Mill bit 750 is inserted into jaws 650. The position of chuck 660 with respect to transmission housing 725 is maintained by bearings 740 and 730 and thrust bushing 708. Mill bit 750 is parallel to saw guide post 812.

Figure 23A:
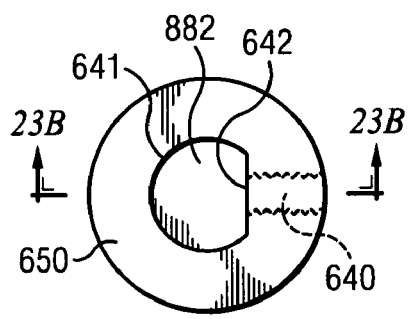
FIG. 23a is a top view of the top of the chuck of an alternate saw embodiment.
Figure 23B:
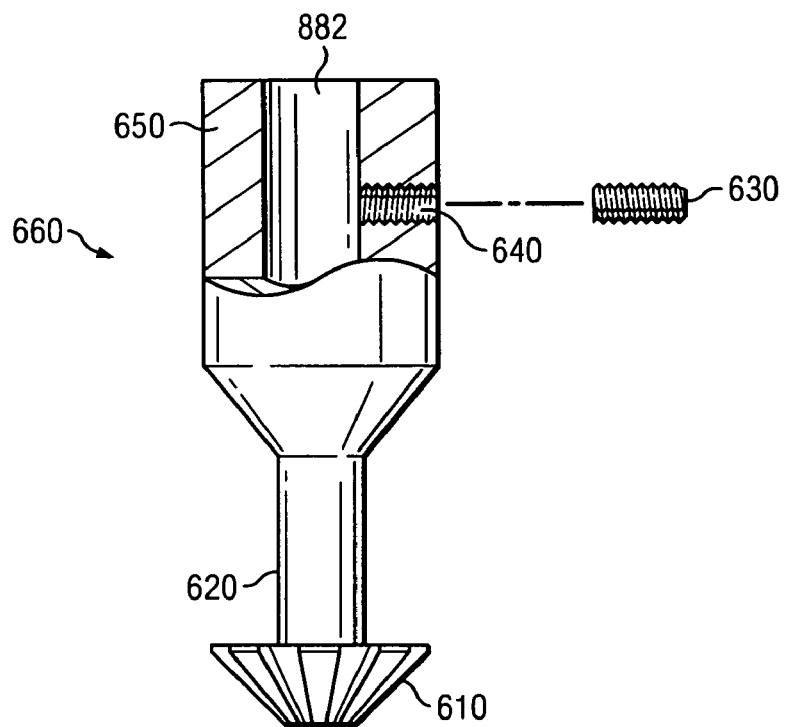
FIG. 23b is a partial cut away side view of the chuck of an alternate saw embodiment.

FIGS. 23*a* and 23*b* are further illustrations of chuck 660. Bevel gear 610 is integrally connected to bearing shaft 620. Bearing shaft 620 is integrally connected to jaws 650. Jaws 650 are approximately cylindrical in shape with mill bit hole 882 removed which is same shape as end of mill bit 750. Jaws 650 have set screw hole 640. Set screw hole 640 is threaded to mate with set screw 630.

In one embodiment, mill bit hole 882 has flat surface 642 and semicircular surface 641. Set screw hole 640 is centered along the latitudinal axis of flat surface 642.

Referring to FIGS. 22a and 22b, mounting plate 720 is attached to transmission housing 725 through use of screws 722. Mounting plate 720 has set screw hole 770. Set screw hole 770 allows access to set screw 630 for locking mill bit 750 into chuck 660. Mounting plate 720 has bit stop 836 and mounting bracket 835.

Referring now to FIG. 22b, guide body 795 includes horizontal stop 780 and vertical stop 790. Horizontal stop 780 extends from top 782 of guide body 795 and has horizontal surface 787. Vertical stop 790 is aligned with bottom 783 of guide body 795. Vertical stop 790 and horizontal stop 780 cooperate with bit stop 836 to limit the rotation of the transmission housing and the mill bit to 90 degrees between a vertical position and a horizontal position.

When handle 817 is turned counter-clockwise with respect to the longitudinal axis of guide body 795, bit stop 836 is rotated counterclockwise until bit stop 836 abuts saw guide vertical stop 790. Mill bit 750 will be substantially perpendicular to guide body 795 when bit stop 836 abuts guide vertical stop 790. When handle 817 is rotated clockwise with respect to the longitudinal axis of guide body 795, bit stop 836 will rotate clockwise until bit stop 836 abuts horizontal stop 780. When bit stop 836 abuts horizontal stop 780, mill bit 750 will be substantially parallel to guide body 795.

In use, mill bit 750 is inserted into mill bit hole 882. Set screw 630 is advanced through set screw hole 770, into set screw hole 640 until abuts mill bit 750. Saw 802 is then inserted into a distractor as described in previous embodiment. Switch 840 activates motor 860 by connecting it to a power source, which rotates transmission shaft 700 and bevel gear 735. Rotation of bevel gear 735 rotates bevel gear 610 and chuck 660, which causes mill bit 750 to rotate. Handle 817 is manually rotated counterclockwise around the longitudinal axis of guide body 795 which rotates mill bit 750 in relation to the longitudinal axis of guide body 795 and exposing mill bit 750 to vertebrae in order to cut a slot in the vertebra. After a slot has been cut, handle 817 is manually rotated clockwise around the longitudinal axis of guide body 795 until mill bit 750 is substantially parallel to latitudinal axis of guide body 795. Switch 840 then deactivates motor 860. The procedure is repeated for cutting additional slots in vertebra as previously described with manual saw embodiment.

Mill bit 750 has a diameter of between approximately 1 mm and 5 mm and a length of between 0.6 cm and 3.9 cm and corresponds to the size of the radial anchors of the implant being inserted between vertebra. Multiple size mill bits are included and the appropriate size is inserted to correspond to size needed for the particular implant.

In some spondylolisthesis conditions, the relocation of vertebra may either be minor or unnecessary, however the natural tilt and location between two adjacent vertebrae needs to be maintained and stabilized. For this type of condition, another embodiment of an implant and instrumentation are used which includes a tapering to match the tilt of the vertebrae.

Figure 24A:
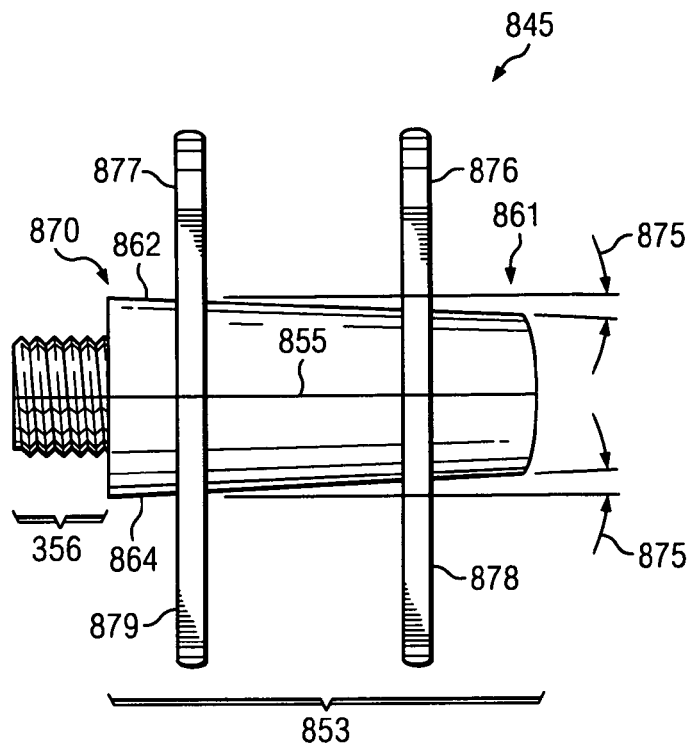
FIG. 24a is a side view of an implant in another embodiment of the invention.
Figure 24B:
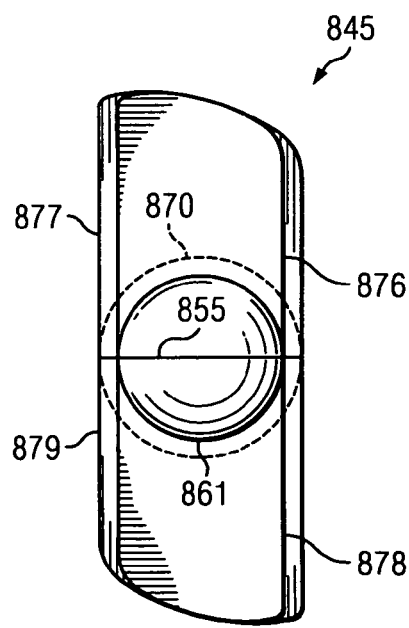
FIG. 24b is an end view of an implant in another embodiment of the invention.

FIGS. 24a and 24b are illustrative of an additional preferred embodiment of a tapered implant. Implant 845 has an implant body 853 that is tapered creating a frustroconical shape. Implant body 853 has implant body front end 870 and back end 861. The cross-section of front end 870 is circular. The cross-section of back end 861 is circular. Degree of tapering 875 is the degree by which the tapering occurs along implant body 853 and ranges between approximately 2 and 10 degrees.

Implant body 853 has two halves, upper half 862 and lower half 864. Upper half 862 and lower half 864 meet at implant seam 855.

Figure 25:
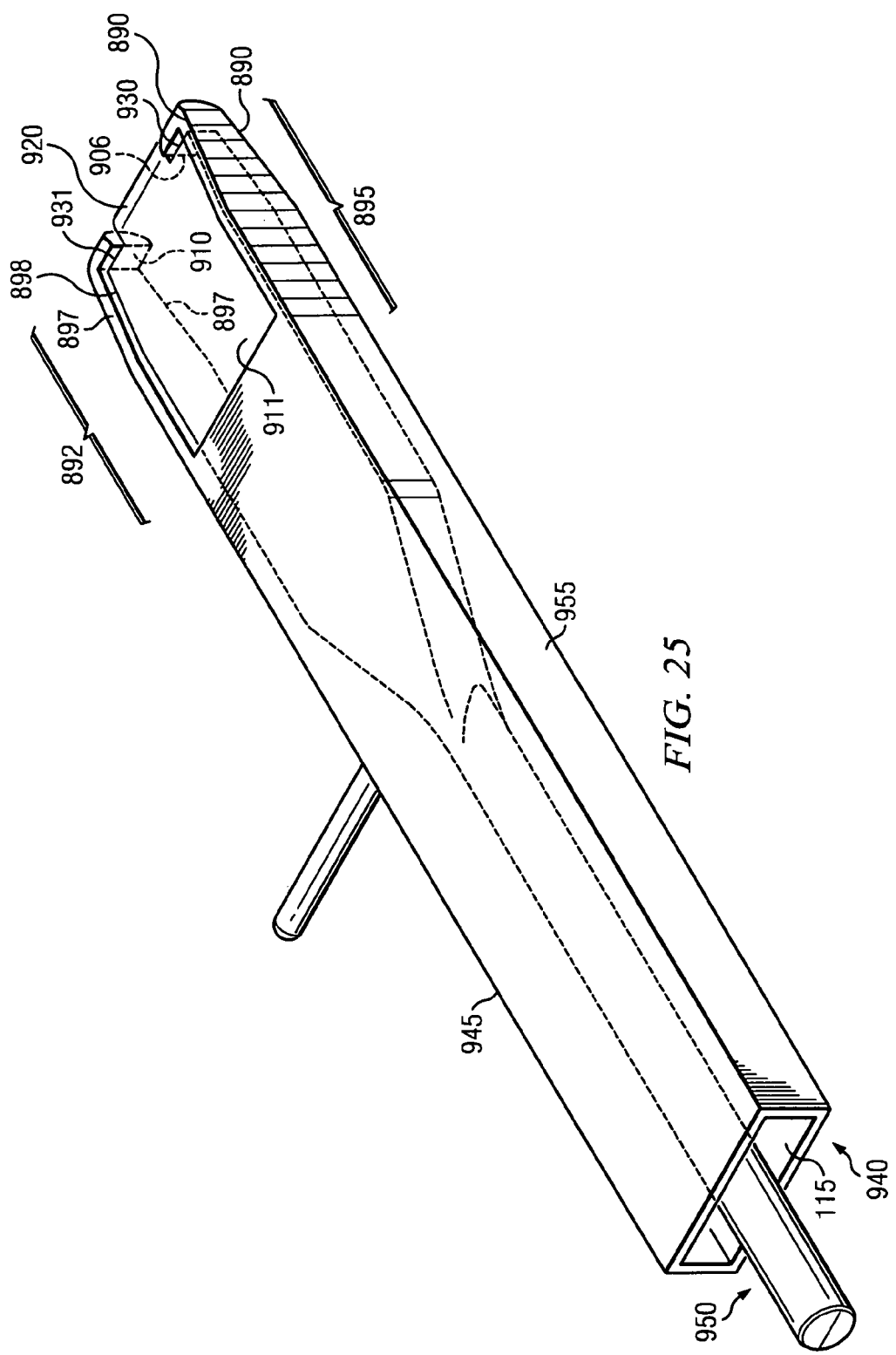
FIG. 25 is an isometric view of an impactor in conjunction with a distractor of another embodiment of the invention.

Implant body 853 has radial anchors 876 and 877 on upper half 862 and radial anchors 878 and 879 on lower half 864. Radial anchors 876, 877, 878, and 879 are substantially perpendicular to implant seam 855. Radial anchors 878 and 876 have less surface area than radial anchors 877 and 879, and are reduced in area to conform to a modified distractor as shown in FIG. 25. Other features of implant 845 are similar to those previously described in other embodiment.

FIG. 25 is illustrative of other preferred embodiments for a distractor and impactor to be used with tapered implant 845. FIG. 25 illustrates impactor 950 within distractor 940.

Distractor 940 has distractor arm 895 and distractor arm 892. Distractor arm 895 extends longitudinally from side 955 of distractor 940. Distractor arm 892 extends longitudinally from side 945 of distractor 940. Distractor arm 895 has taper arm 890 which tapers both the top and bottom between an approximate 2 and 10 degree angle along the longitudinal axis of distractor arm 895. Taper arm 897 on distractor arm 892 tapers the height from both the top and the bottom between an approximate 2 and 10 degree angle. Taper arm 897 includes distractor stop 910 and taper arm 890 has distractor stop 906. The remaining features of distractor 940 are consistent with previously disclosed embodiment of distractor.

Impactor 950 has impactor head 911. The posterior end of impactor head 911 has tapered end 898. Tapered end 898 has between approximately 2 and 10 degrees of taper along the longitudinal axis of impactor head 911. Tapered end 898 ends in impactor seat 920 and on either side of impactor seat 920 are stop surfaces 930 and 931. The tapering of tapered end 898 corresponds to the tapering of taper arm 890 and taper arm 897 such that stop surfaces 930 and 931, when fully inserted, touch distractor stop 906 and distractor stop 910 and do not extend beyond edges of distractor arms 892 or 895. The remaining features of impactor 950 are consistent with previously disclosed embodiment of impactor.

As disclosed with prior embodiments, with the tapered implant system, the implant, distractor, impactor, and other parts necessary to complete the disclosed surgery have a variety of heights depending on the patient and the condition to be resolved.

Figure 26A:
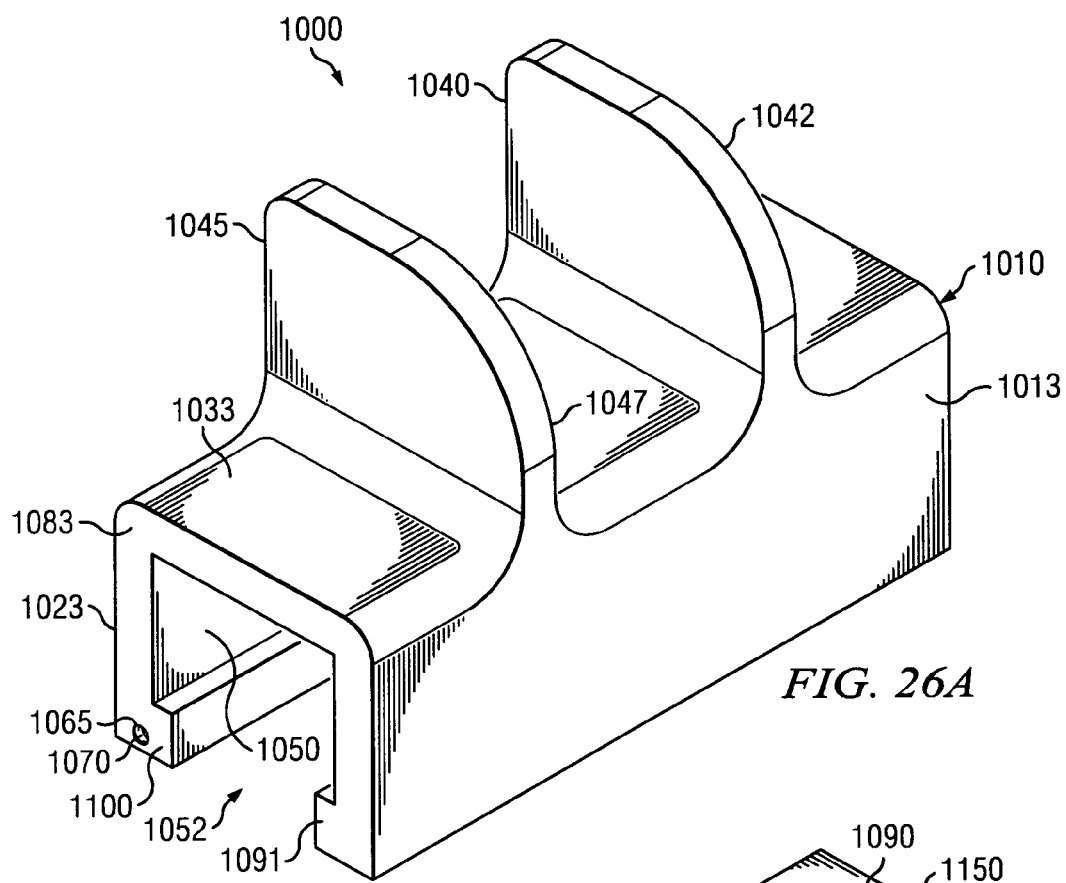
FIG. 26 is an exploded isometric view of the implant of another preferred embodiment of the invention.
Figure 26B:
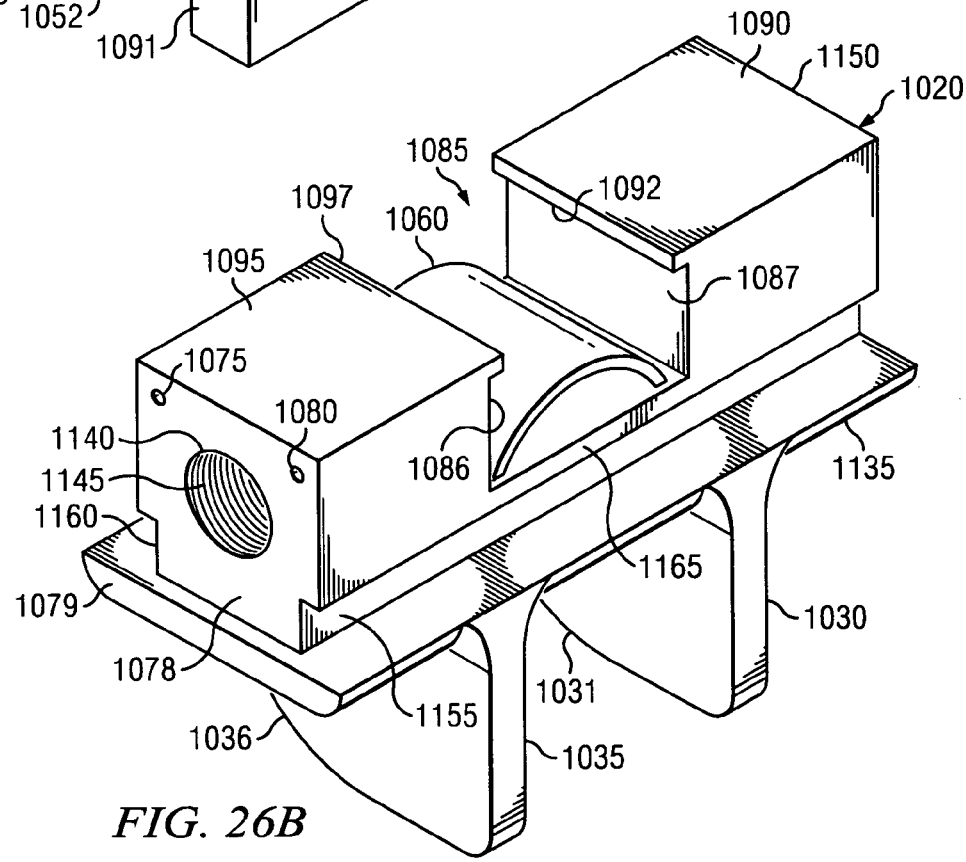
Figure 26C:
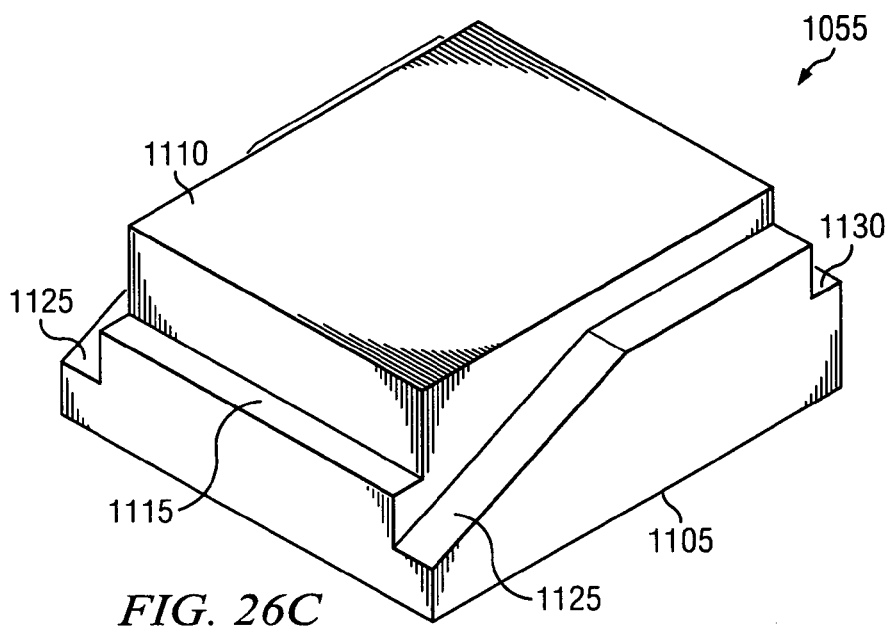

FIGS. 26 A, B, C and 27 are illustrative of an additional preferred embodiment of an implant with a different locking mechanism.

Implant 1000 has an upper half 1010 and a lower half 1020. Upper half 1010 has a generally rectangular shape and includes integrally formed and parallel planar radial anchors 1040 and 1045. Radial anchor 1045 includes curved surface 1047. Radial anchor 1040 includes curved surface 1042. In other embodiments, the upper half and lower half of the implant may include different numbers of radial anchors. Furthermore, the upper half and lower half of implant 1000 do not necessarily need to include the same number of radial anchors. In embodiments which include different numbers of radial anchors, it will be understood by those skilled in the art that the same number of saw guides must be included on the gate in order to correspond with the number and orientation of the radial anchors.

Upper half 1010 includes upper channel 1050 which extends along its longitudinal axis. Upper channel 1050 is bounded by side wall 1013, side wall 1023, and top wall 1033. Side wall 1013 and side wall 1023 are substantially perpendicular to top wall 1033.

Side wall 1023 includes connection guide 1100 which is substantially perpendicular to side wall 1023 and substantially parallel to top wall 1033.

Side wall 1013 includes connection guide 1091 which is substantially perpendicular to side wall 1013 and substantially parallel to top wall 1033. Gap 1052 exists between connection guide 1100 and connection guide 1091 and traverses the longitudinal axis of upper half 1010.

Side wall 1023 includes thumbscrew hole 1065 located on front end 1083. Thumbscrew hole 1065 includes threads 1070.

Figure 27:
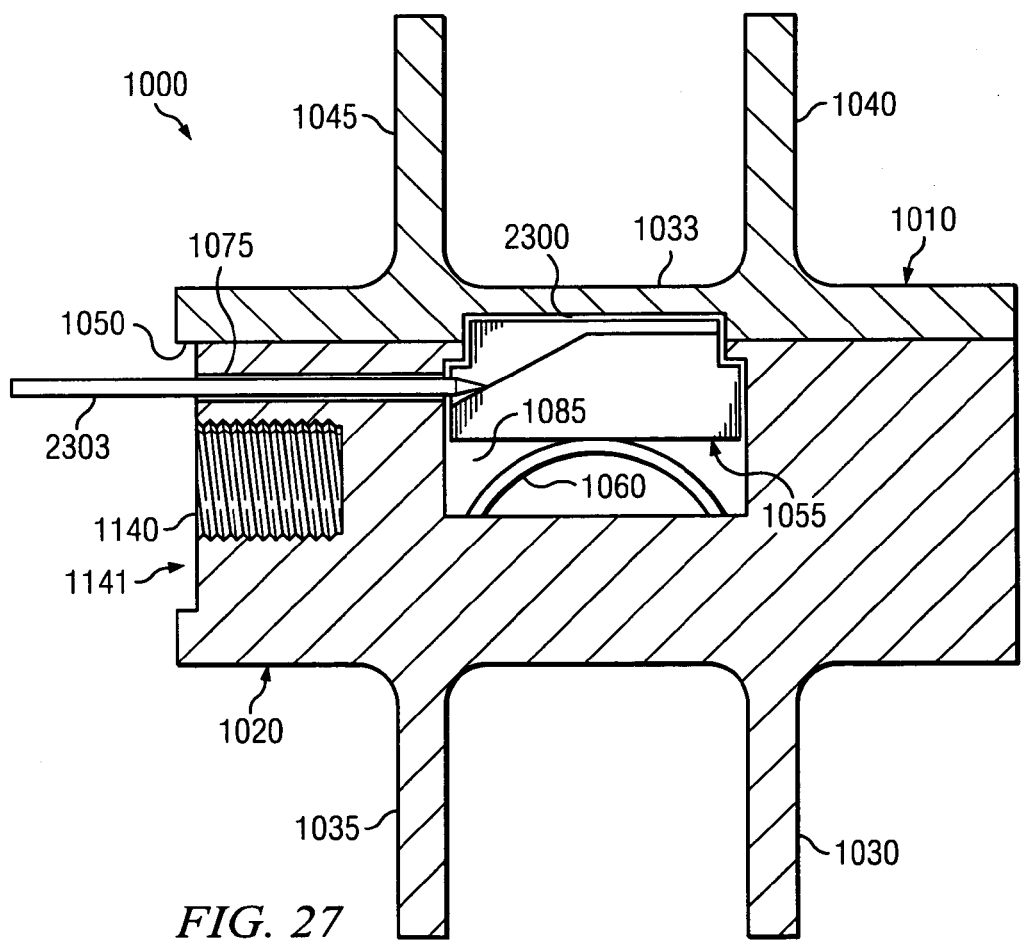
FIG. 27 is a cut away view of the implant of another preferred embodiment of the invention.

As shown in FIG. 27, top wall 1033 includes locking recess 2300. Locking recess 2300 forms a recess in top wall 1033 adjacent to upper channel 1050. Locking recess 2300 is generally centered along the longitudinal axis of upper half 1010.

In the preferred embodiment, upper half 1010 includes a single thumbscrew hole, however, in alternative embodiments upper half 1010 could contain up to four thumbscrew holes located at the corners of upper half 1010. The additional holes accommodate additional thumbscrews to aid in assembly of the implant as will be further described later.

Lower half 1020 includes platform 1135. Platform 1135 includes two parallel planar radial anchors 1030 and 1035. Radial anchors 1030 and 1035 are integrally formed with platform 1135. Radial anchor 1030 includes curved surface 1031. Radial anchor 1035 includes curved surface 1036.

Platform 1135 includes positioning block 1150. Platform 1135 has front end 1079. Positioning block 1150 is located adjacent front end 1079.

Positioning block 1150 includes connecting grooves 1155 and 1160 adjacent platform 1135. Connecting grooves 1155 and 1160 align with and engage connection guides 1091 and 1100.

Positioning block 1150 includes locking arms 1090 and 1095. Locking arms 1090 and 1095 are adjacent locking hollow 1085. Locking hollow 1085 is bounded by sidewalls 1086 and 1087.

Locking arm 1095 includes extension 1097, adjacent to and substantially perpendicular to sidewall 1086. Locking arm 1090 includes extension 1092, adjacent to and substantially perpendicular to sidewall 1087.

Spring 1060 is positioned within locking hollow 1085 between sidewalls 1086 and 1087 adjacent surface bottom 1165. Spring 1060 is shorter than the distance between sidewalls 1086 and 1087 to allow for deflection. Spring 1060 is nonmetallic so as to be MRI compatible. In another preferred embodiment, the spring can be a coil spring fixed to surface bottom 1165.

Locking arm 1095 includes holes 1075 and 1080. Holes 1075 and 1080 intersect locking hollow 1085 on sidewall 1086.

Locking arm 1095 includes bolt hole 1140. Bolt hole 1140 extends through locking arm 1095 but does not extend into locking hollow 1085. Bolt hole 1140 includes threads 1145.

Locking block 1055 fits within locking hollow 1085. Locking block 1055 includes upper section 1110 and lower section 1105. Lower section 1105 includes positioning stop 1115 and positioning stop 1130. Lower section 1105 is capable of vertical movement within locking hollow 1085. Positioning stops 1115 and 1130 interfere with extensions 1097 and 1092 and impede the vertical movement of locking block 1055 at its upper limit.

Lower section 1105 also includes incline section 1125. Incline section 1125 is adjacent upper section 1110 has an incline of between about 10° and about 75°.

Upper section 1110 is integrally formed with lower section 1105 and is approximately centered along the longitudinal axis of lower section 1105. Upper section 1110 fits within locking recess 2300 without significant longitudinal play.

In order to assemble implant 1000, locking block 1055 is positioned adjacent spring 1060 inside locking hollow 1085. Locking block 1055 is depressed until upper section 1110 is aligned horizontally with locking arms 1090 and 1095. Upper half 1010 is connected with lower half 1020 by sliding connection guides 1091 and 1100 into connecting grooves 1155 and 1160. When assembled, upper half 1010 and lower half 1020 form cavity 1141.

FIGS. 28 a, b, c, and d, are illustrative of a preferred embodiment of implements to aid installation of implant 1000 and include reduction rod 2000, reduction bar 2100, thumbscrew 2050 and reduction wheel 2070.

Reduction bar 2100 includes a substantially rectangular cross-section which corresponds to the outside cross-section of implant 1000 when assembled. Reduction bar 2100 includes sides 2115 and 2120, top 2125, bottom 2130, front end 2145 and back end 2150. Torque handle 2110 has circular cross-section and extends at a generally perpendicularly angle from side 2115. Torque handle 2110 is integrally formed with reduction bar 2100.

Reduction bar 2100 includes channels 2135 and 2140 which traverse the longitudinal span of reduction bar 2100. Channels 2135 and 2140 have substantially circular cross-ssections. The axis of channel 2135 is generally centered on the longitudinal axis of the reduction bar. The axis of channel 2140 is offset from the axis of channel 2135.

Back end 2150 includes implant spacer 2155. Implant spacer 2155 forms a raised stanchion. The implant spacer is designed to rest within cavity 1141 shown in FIG. 27.

Reduction rod 2000 includes a cylindrical section 2010 and hexagonal section 2040. Hexagonal section 2040 is integrally formed with cylindrical section 2010. In one preferred embodiment, hexagonal section 2040 includes etching 2033 at predetermined intervals the etchings are substantially perpendicular to the logistical axis of the reduction rod. Cylindrical section 2010 includes back end 2025 and front end 2030. Back end 2025 includes threads 2020. Front end 2030 includes threads 2035. Cylindrical section 2010 is sized to fit within channel 2135.

Thumbscrew 2050 has cylindrical section 2023 and knurled thumbscrew head 2065. Cylindrical section 2023 is sized to fit within channel 2140. Cylindrical section 2023 includes threads 2060. Thumbscrew head 2065 is integrally formed with cylindrical section 2023. Thumbscrew head 2065 is substantially cylindrical in shape and has a diameter greater than cylindrical section 2023.

Reduction wheel 2070 includes integrally formed cylindrical section 2090 and conical section 2095. Conical section 2095 is coaxial with cylindrical section 2090. Coaxial channel 2075 extends through cylindrical section 2090 and conical section 2095. Channel 2075 is circular and includes threads 2080. Threads 2080 mate with threads 2035 of reduction rod 2000.

In alternate embodiments of upper half 1010, more than one thumbscrew hole is provided, and reduction bar 2100 includes a corresponding number of channels to accommodate the thumbscrew holes. Additional thumbscrews 2050 are provided, corresponding to the number of thumbscrew holes.

In practice, the vertebrae are prepared and slots are cut as previously discussed. Distractor 110 (as shown in FIG. 2) remains between the vertebrae.

Implant 1000 is prepared by sliding upper half 1010 over lower half 1020 until a predetermined spacing between the radial anchors is achieved. The predetermined spacing is based on the distance that the vertebrae must be moved to correct their alignment.

Guide block 460, as shown in FIG. 15, is guided onto reduction bar 2100 such that guide block 460 is between torque handle 2110 and back end 2150. The diameter of guide hole 470 should provide sufficient clearance for rotation and transition of reduction bar 2100 without excessive play.

Reduction bar 2100 is placed adjacent to implant 1000 such that implant spacer 2155 is properly aligned with implant 1000.

Thumbscrew 2050 is inserted into channel 2140. Channel 2140 is aligned with thumbscrew hole 1065 on upper half 1010. Threads 2060 are advanced into threads 1070 until upper half 1010 is adjacent to back end 2150, thus securing upper half 1010 to reduction bar 2100.

Reduction rod 2000 is then inserted into channel 2135, which is aligned with bolt hole 1140, until threads 2020 meet bolt hole 1140. Threads 2020 are advanced into threads 1145 until lower half 1020 is secured to reduction rod 2000.

Reduction wheel 2070 is connected to reduction rod 2000. Conical section 2095 slides over hexagonal section 2040 until it engages front end 2030. Threads 2080 are engaged with threads 2035. Reduction wheel 2070 is rotated until the desired marking becomes visible at the top of reduction wheel 2070 corresponding to the amount of adjustment needed between the vertebrae, or until conical section 2095 abuts reduction bar 2100.

In another preferred embodiment, upper half 1010 is aligned with reduction bar 2100 and attached to reduction rod by thumbscrew 2050. Lower half 1020 is then connected to upper half 1010 by engaging connection guides 1100 and 1091 with connecting grooves 1160 and 1155 until the appropriate spacing exists between the radial anchors. Reduction rod 2000 is then placed through channel 2135 and threaded into bolt hole 1140. Reduction wheel 2070 is connected to front end 2030 of reduction rod 2000. Reduction wheel 2070 is then rotated to complete and secure the proper positioning of upper half 1010 in relation to lower half 1020.

In another preferred embodiment, reduction wheel 2070 can be connected to reduction rod 2000 prior to reduction rod 2000 being inserted into channel 2135.

Implant 1000 is placed within distractor channel 115 and advanced within distractor channel 115 until guide block bottom 465 is inserted into distractor channel 115. Guide block bottom 465 is advanced within distractor channel 115 until guide block top 475 abuts anterior end 111 of distractor body 99 and implant 1000 is placed between the vertebrae where radial anchors 1045, 1040, 1030, and 1035 align with the cut slots. Implant 1000 is rotated by use of the reduction bar 2100 so that radial anchors 1045, 1040, 1030, and 1035 enter their respective slots in the vertebrae. Reduction bar 2100 is sized so as to allow rotation within distractor channel 115.

To adjust the vertebrae into proper position, reduction bar 2100 is held in position by use of torque handle 2110. Reduction wheel 2070 is rotated such that reduction rod 2000 is moved anteriorly and lower half 1020 is aligned with upper half 1010. In one embodiment, for each complete 360 degrees turn of reduction wheel 2070, lower half 1020 will move 1 mm with respect to upper half 1010. When upper half 1010 and lower half 1020 are aligned, spring 1060 pushes locking block 1055 vertically into locking recess 2300 thus locking the upper half 1010 and lower half 1020 in place. In the preferred embodiment, when implant 1000 is aligned, back end 2030 of reduction rod 2000 will be horizontally aligned with the surface of cylindrical section 2090.

When implant 1000 is aligned and locked in place, reduction wheel 2070 is unthreaded from reduction rod 2000. Reduction rod 2000 is unthreaded from bolt hole 1140. Thumbscrew 2050 is unthreaded from thumbscrew hole 1065 and reduction bar 2100 is removed from implant 1000 leaving implant 1000 in place. Guide block 460 and distractor 110 are then removed.

In the event that implant 1000 needs to be adjusted, upper half 1010 and lower half 1020 can be unlocked. Referring again to FIG. 27, pin 2303 is inserted through holes 1075 and/or 1080. Pin 2303 engages the incline section and forces locking block 1055 downward into locking hollow 1085 thus allowing upper half 1010 to move in relation to lower half 1020.

After alignment of the vertebrae, an interbody arthodesis is performed on each side of implant 1000 and between remaining distended disk as discussed with prior embodiments.

FIGS. 19a and 19b illustrate one embodiment of plate 540 which can be used with the different embodiments of implants, including implant 1000, and has previously been discussed.

Figure 29A:
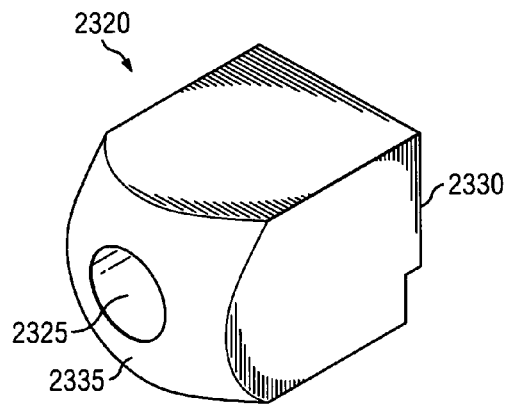
FIG. 29a is an elevated view of a spacer of a preferred embodiment of the invention.
Figure 29B:
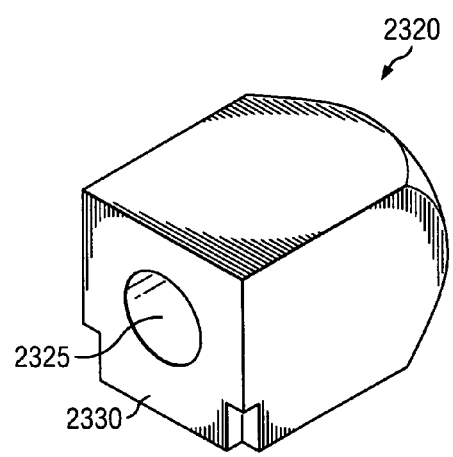
FIG. 29b is an elevated view of a spacer of a preferred embodiment of the invention.

FIGS. 29a and 29b illustrate one embodiment of spacer 2320. Spacer 2320 has front 2335 and back 2330. Back 2330 has a similar shape as locking arm 1095. Front 2335 has a curvature which corresponds to curvature of back of plate 540 (shown in FIG. 19a). Spacer 2320 has hole 2325 which has diameter similar to bolt hole 1140 on implant 1000. Hole 2325 extends through the longitudinal axis of spacer 2320.

Figure 30:
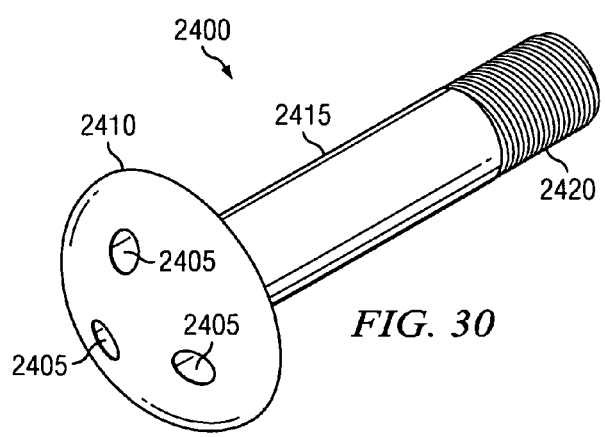
FIG. 30 is an isometric view of a bolt of a preferred embodiment of the invention.

FIG. 30 illustrates one embodiment of bolt 2400. Bolt 2400 includes elliptical bolt head 2410. Diameter of bolt head 2410 is between about 0.65 cm and 3.4 cm preferably. Bolt head 2410 contains spanner holes 2405. The diameter of bolt body 2415 should be approximately the same as diameter of bolt hole 1140. Bolt body 2415 has threads 2420 which engage bolt hole 1140 in implant 1000. The length of bolt body 2415 should be between 0.2 cm and 8 cm. The dimensions are suggested, but not critical.

In use, plate 540, spacer 2320, and bolt 2400 are used to secure implant 1000 in position. Bolt body 2415 is placed through plate nut hole 560. Spacer 2320 is engaged with bolt body 2415. Front 2335 of spacer 2320 is adjacent plate 540. Threads 2420 are threaded into bolt hole 1140. Back 2330 is aligned with and adjacent to positioning locking arm 1095. Plate 540 is then properly aligned and secured to the vertebrae as discussed with prior embodiments.

Reduction bar 2100, reduction rod 2000, thumbscrew 2050, and reduction wheel 2070 are preferably made from titanium, stainless steel, or other materials which are readily sterilized or from a rigid plastic such as PVC which may be disposed of after use.

Implant 1000, spacer 2320, and bolt 2400 in the preferred embodiment are made from titanium, stainless steel, alloys such as titanium allow, or other materials which are easily sterilizable. Implant 1000 or parts thereof, may also be made from composite materials such as synthetic bone. Some composites or synthetic bone products include demineralized bone matrix, collagen, ceramics, cements, and polymers, such as silicone and some acrylics and include products such as Vitoss, Cortoss, Rhakoss, Pro Osteon, and Gu-Bang.

As with other embodiments, different size implants, reduction bars, reduction rods, thumbscrews, reduction wheels, plates, spacers, and bolts are included to best fit the patient's individual vertebrae and needed alignment. Further, different length spacers can also be included to account for the difference lengths between the outside of the vertebrae and the implant.

It will be appreciated by those skilled in the art that changes could be made to the embodiments described above without departing from the broad inventive concept. It is understood, therefore, that this invention is not limited to the particular embodiments disclosed, but it is intended to cover modifications within the spirit and scope of the present invention as defined by the appended claims.

The invention claimed is:

1. An implant for changing an alignment between two vertebrae and maintaining an alignment position comprising:
   a first body having a first longitudinal axis, a first channel, a first connecting joint, a second connecting joint, and a first set of radial anchors;
   the first channel having a receiving recess;
   the first set of radial anchors radially extending generally perpendicularly from the first body;
   a second body having a second longitudinal axis, a positioning block, a first receiving joint, a second receiving joint, and a second set of radial anchors;
   the second set of radial anchors radially extending generally perpendicularly from the second body;
   the first body and the second body slidingly connected by the first connecting joint being located in the first receiving joint and the second connecting joint located in the second receiving joint;
   the first body and the second body connected to form an implant body;
   the positioning block located within the first channel;
   the positioning block having a locking recess;
   the locking recess containing a spring and a locking block;
   the spring biasing the locking block and the locking recess;
   the first set of radial anchors and the second set of radial anchors being generally parallel;
   the first set of radial anchors having a first set of corners and a second set of corners;
   the second set of radial anchors having a third set of corners and a fourth set of corners; and,
   wherein the first body and the second body, in the alignment position, are aligned such that the locking block is movable into the receiving recess by the spring in order to maintain the alignment position.

2. The implant of claim 1 further comprising:
   a reduction bar removably connected to the first body;
   a reduction rod, rotatably positioned adjacent the reduction bar, removably connected to the second body; and,
   a threaded handle, adjacent the reduction bar and threaded onto the reduction rod, for advancing the first body with respect to the second body.

3. The implant of claim 1 wherein the first set of radial anchors includes a first plurality of anchors and the second set of radial anchors includes a second plurality of anchors.

4. The implant of claim 1 wherein the positioning block has a first extension and a second extension; and wherein the first extension and the second extension extend substantially perpendicular to the positioning block and into the locking recess.

5. The implant of claim 1 wherein:
   the locking block has an anterior end, a posterior end, and an upper ridge;
   the anterior end having a first stop and the posterior end having a second stop;
   the upper ridge being latitudinally centered on the locking block and having a width less than the locking block.

6. The implant of claim 5 wherein the locking block has a set incline, wherein the set incline begins at the anterior end and inclines upward toward the posterior end.

7. The implant of claim 1 wherein the spring is one of the group of coil or leaf spring.

8. A system for correcting alignment between two vertebrae caused by spondylolisthesis comprising:
   a distractor having a distractor body with a hollow chamber along a distractor body longitudinal axis, an anterior end, a posterior end having a first longitudinal extension and a second longitudinal extension which extend from the distractor body in the direction of the distractor body longitudinal axis, the first longitudinal extension having a first stop surface perpendicular to the first longitudinal extension and extending parallel to the distractor body, the second longitudinal extension having a second stop surface perpendicular to the second longitudinal extension and extending parallel to the distractor body, a gap between the first stop surface and the second stop surface, a measurement scale along the first longitudinal extension, and a torque handle perpendicularly attached to the distractor body;
   an impactor having an impactor handle, an impactor body having a longitudinal axis, a latitudinal axis, an impactor body anterior end, and an impactor body posterior end, the impactor handle being centered on the latitudinal axis of the impactor body anterior end, an impactor seat centered along the latitudinal axis of the impactor body posterior end;
   the impactor seat fits within the gap on the distractor;
   a gate having a gate longitudinal axis, a gate latitudinal axis, a distractor end and a guide end, the distractor end having an insertion conduit and having a distractor stop, the guide end having a guide conduit, a top side, a bottom side, a right side, a left side, a gate anterior end, a first set of guide slots from a first centerline of the right side to a second centerline of the bottom side and parallel to the gate anterior end, a second set of guide slots from a third centerline of the left side to a fourth centerline of the top side and parallel to the gate anterior end, a first side slot along the first centerline of the right side and ductedly connected to the first set of guide slots and terminating in a first end, a second side slot along a second centerline of the left side and ductedly connected to the second set of guide slots and terminating in a second end, the first set of guide slots having a first set spacing and the second set of guide slots having a second set spacing, the first set spacing related to the second set spacing by a third set spacing;
   a saw unit with a saw longitudinal axis, the saw unit having a saw handle joined to a spindle connected to a saw blade, a saw guide body, and a saw guide projection, the saw guide projection joined to the saw handle at an angle generally perpendicular to the saw longitudinal axis, the saw guide body further having a longitudinal pivot hole coaxial with the saw longitudinal axis, the saw guide body further having a horizontal blade stop and a vertical blade stop, the spindle rotatively mounted in the longitudinal pivot hole, the saw blade having a saw blade longitudinal axis parallel to the saw guide projection and movable between a stoppage position dictated by the horizontal blade stop and an operational position dictated by the vertical blade stop;
   an implant with a first body having a first body longitudinal axis, a first channel, a first body outer surface, a first threaded hole, and a first connection joint, the first channel having a receiving recess, and a second body having a second body longitudinal axis, a second body outer surface, a positioning block, and a second connection joint, the first body and the second body slidably connected by the first connection joint and the second connection joint forming a rectangular body wherein the positioning block is located within the first channel, a second threaded hole located on an anterior end of the positioning block, the positioning block having a locking recess in which a spring and a locking block is located, the first body having a first set of radial anchors radially extending and generally perpendicular to the first body longitudinal axis from the first body outer surface and the second body having a second set of radial anchors radially extending from the second body outer surface and generally perpendicular to the second body longitudinal axis;

an inserter having a first inserter chamber and a second inserter chamber and an inserter torque handle attached generally perpendicular to the inserter, both the first inserter chamber and the second inserter chamber extending through an inserter longitudinal axis;

a screw having a screw connection end and a screw head, and the screw connection end threaded;

the screw connection end fitting within the first threaded hole;

a rod having a cylindrical section and a hexagonal section, the cylindrical section having a rod anterior end and a rod posterior end, the rod anterior end and the rod posterior end are threaded;

the rod posterior end fitting within the second threaded hole;

a reduction wheel having a cylindrical section and a reduction wheel chamber, the reduction wheel chamber generally centrally located within the cylindrical section;

the reduction wheel chamber fitting over the rod anterior end;

a bolt having a bolt head and a bolt body, the bolt body being generally perpendicular to the bolt head, the bolt body being threaded;

a spacer with a spacer chamber;

a plate having a plate hole, a plurality of screw holes, and a face, the plate hole being centered in the face; and wherein the implant has an alignment position, in which the locking block is located within the receiving recess.

9. The system of claim 8 wherein the first set of radial anchors and the second set of radial anchors include a predetermined number of radial anchors, said predetermined number being one of the group of one, two, three, four and five.

10. The system of claim 8 wherein the measurement scale has a plurality of markings spaced 1 mm apart.

11. The system of claim 8 wherein the saw unit includes a handle housing, a motor rigidly mounted in the handle housing, a drive shaft extending from and driven by the motor, the drive shaft extending through a hole in the handle housing and the spindle, a transmission housing rigidly attached to the spindle, a transmission located within the transmission housing, the transmission operatively connected to the drive shaft and to a chuck; the chuck releasably fixed to a mill bit; the transmission housing further comprising an index means for limiting the rotation of the transmission housing with respect to the guide body.

12. The system of claim 8 further comprising a set of gates wherein each gate in the set of gates has a different third set spacing.

13. The system of claim 8 further comprising a set of distractors, a set of impactors, a set of saw units, a set of saw guide bodies, and a set of implants wherein each distractor, impactor, saw unit, saw guide body and implant of the set of distractors, the set of impactors, the set of saw units, the set of saw guide bodies, and the set of implants has a unique height.

14. The system of claim 8 further comprising a set of spacers, each of the set of spacers having a unique length.

15. An implant for changing an alignment between two vertebrae comprising:
 a first body member having a first central longitudinal channel adjacent a first connection joint and a central locking recess;
 a first set of radial anchors extending from the first body member generally perpendicular to the first central longitudinal channel;
 a second body member having a positioning block adjacent a second connection joint,
 a second set of radial anchors extending from the second body generally perpendicular to the positioning block;
 the first body member and the second body member slidingly connected by the first connection joint and the second connection joint whereby the positioning block is located within the first central longitudinal channel;
 the positioning block including a locking chamber;
 a locking block and a spring included in the locking chamber; and
 whereby when the implant is located between the two vertebrae and the second body member and the first body member are aligned such that the locking block is moved into the central locking recess by the spring, the alignment between the two vertebrae is corrected.

16. The implant of claim 15 wherein the positioning block includes a threaded drive screw hole.

17. The implant of claim 15 wherein the first set of radial anchors and the second set of radial anchors include a predetermined number of radial anchors, said predetermined number being one of the group of one, two, three, four and five.

18. The implant of claim 15 wherein the first body member includes a first thumbscrew hole that is threaded.

19. The implant of claim 15 wherein the first body member includes a second thumbscrew hole that is threaded.

20. The implant of claim 15 wherein the spring is one of the group of coil or leaf spring.

21. The implant of claim 15 wherein the positioning block includes a first pin hole and a second pin hole, the first pin hole and the second pin hole intersect with the locking chamber.

22. The implant of claim 15 wherein:
 the locking block has an anterior end, a posterior end, and an upper ridge;
 the anterior end having a first stop and the posterior end having a second stop;
 the upper ridge being latitudinally centered on the locking block and having a width less than the locking block.

23. The implant of claim 22 wherein the locking block has a set incline, wherein the set incline begins at the anterior end and inclines upward toward the posterior end.

24. The implant of claim 23 wherein the positioning block includes a first extension and a second extension;
 the first extension and the second extension extending substantially perpendicular to the positioning block and into the locking chamber.

* * * * *